(12) United States Patent
Fryd et al.

(10) Patent No.: US 7,060,372 B2
(45) Date of Patent: Jun. 13, 2006

(54) POLYMERS HAVING ATTACHED LUMINESCENT METAL COMPLEXES AND DEVICES MADE WITH SUCH POLYMERS

(75) Inventors: Michael Fryd, Philadelphia, PA (US); Vladimir Grushin, Hockessin, DE (US); Norman Herron, Newark, DE (US); Mookkan Periyasamy, Wilmington, DE (US); Viacheslav A. Petrov, Hockessin, DE (US); Nora Sabina Radu, Landenberg, PA (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/012,425

(22) Filed: Dec. 14, 2004

(65) Prior Publication Data

US 2005/0158581 A1 Jul. 21, 2005

Related U.S. Application Data

(62) Division of application No. 09/974,113, filed on Oct. 9, 2001, now Pat. No. 6,869,693.

(60) Provisional application No. 60/238,974, filed on Oct. 10, 2000.

(51) Int. Cl.
C09K 11/06 (2006.01)
H05B 33/14 (2006.01)
C08G 83/00 (2006.01)

(52) U.S. Cl. .................. 428/690; 313/504; 257/40; 257/E51.027; 257/E51.043; 252/301.35; 528/166; 528/210; 528/219

(58) Field of Classification Search ............... None
See application file for complete search history.

(56) References Cited

U.S. PATENT DOCUMENTS

| 4,985,053 A * | 1/1991 | Sugie ............................. 96/14 |
| 5,118,405 A | 6/1992 | Kaneko et al. |
| 5,281,489 A | 1/1994 | Mori et al. |
| 5,432,014 A * | 7/1995 | Sano et al. .................. 428/690 |
| 5,504,183 A | 4/1996 | Shi et al. |
| 5,580,527 A | 12/1996 | Bell et al. |
| 5,653,914 A | 8/1997 | Holmes et al. |
| 5,681,659 A | 10/1997 | Shi et al. |
| 5,895,717 A | 4/1999 | Cao et al. |
| 6,316,130 B1 * | 11/2001 | Heuer et al. ................. 428/690 |
| 6,545,159 B1 | 4/2003 | Lee et al. |
| 6,565,994 B1 | 5/2003 | Igarashi |
| 2002/0028347 A1 | 3/2002 | Marrocco, III et al. |
| 2002/0193532 A1 | 12/2002 | Ikehira et al. |
| 2003/0091862 A1 | 5/2003 | Tokito et al. |
| 2004/0265253 A1 * | 12/2004 | Seo et al. ..................... 424/63 |

FOREIGN PATENT DOCUMENTS

| EP | 0556005 B1 | 4/1996 |
| EP | 0744451 B1 | 7/1999 |
| EP | 0969532 A2 | 1/2000 |
| WO | WO 02/02714 A2 | 1/2002 |

OTHER PUBLICATIONS

Aguiar, M. et al, Light-Emitting Polymers with Pendant Chromophoric Groups. 2. Poly[styrene-co-(p-(stllbenylmethoxy)styrene)]. Macromolecues, 1996, 3161-3166, 29, American Chemical Society.

Meier, Martin et al., Heterolayer light-emitting diodes based on new oxadiazole polymers, Synthetic Metals, 1996, 95-99, 76, Elsevier Science S.A.

Cacialli, F. et al., Light-emitting diodes based on poly(methacrylates) with distyrylbenzene and oxadiazole side chains, Synthetic Metals, 1996, 161-168, 75, Elsevier Science S.A.

Li, Xiao-Chang et al., A blue light emitting copolymer with charge transporting and photo-crosslinkable functional units, Synthetic Metals, 1997, 437-438, 84, Elsevier Science S.A.

Aguiar, M. et al., Light-Emitting Polymers with Pendant Chromophoric Groups. 1. Poly(stilbenyl-p-methoxystyrene), Macromolecules, 1995, 4598-4602, 26, American Chemical Society.

Hesemann, Peter et al., A Blue Light Emitting Polymer with Phenylenevinylene Segments in the Side-Chains, Advanced Materials, 1995, 388-390, 7(4), VCH Verlagsgesellschaft mbH.

Zhao, Dongxu et al., Organic Light-Emitting Diode using Ev3+ Polymer Complex as an Emitter, Japanese Journal of Applied Physics, Jan. 15, 1999, L46-L48, vol. 36, Pt. 2, No. 1A/B.

Yang, Mujie et al., Monochromatic-Red-Light Emission of Novel Copolymers Containing Carbazole Units and Europlum-Acrylate Complexes, Journal of Polymer Science: Part A: Polymer Chemistry, 2000, 3405-3411, vol. 38, John Wiley & Sons, Inc.

Hiroo, Miyamoto, Patent Abstracts of Japan, Luminescent Material and Organic El Element By Using The Same, Jul. 25, 2000, Publ. No. 2000204364, Oki Electric Ind Co Ltd.

Djurovich, Peter I. et al., Ir(III) Cyclometalated Complexes As Efficient Phosphorescent Emitters in Polymer Blend and Organic LEDs, Polymer Preprints, 2000, 770-771, 41(1).

(Continued)

*Primary Examiner*—Marie Yamnitzky

(57) ABSTRACT

The present invention is generally directed to a polymeric metal complex comprising a polymeric material having a plurality of a first-type functional groups, wherein at least a portion of the functional groups are coordinated to at least one metal containing complex, polymeric-metal complex salts comprising at least one polymeric material having a plurality of first-type functional groups having a charge, and at least one metal complex having an opposite charge. It further relates to devices that are made with the polymeric metal complex or the polymeric-metal complex salt.

3 Claims, 1 Drawing Sheet

OTHER PUBLICATIONS

Yang, Moon-Jae et al., Use of Poly(9-vinylcarbazole) as Host Material for Iridium Complexes in High Efficiency Organic Light-Emitting Devices, Japanese Journal of Appl. Phys., Aug. 1, 2000, L628-L829, vol. 39, No. 6A, The Japan Society of Applied Physics.

Chan, Wai Kin et al., Light-emitting multifunctional rhenlum (I) and ruthenium (II), 2,2'-blpyridyl complexes with bipolar character, Applied Physics Letters, Dec. 1999, 3920-3922, vol. 75, No. 25, American Institute of Physics.

Sacksteder, Louann et al., Long-Lived, Highly Luminescent Rhenium (I) Complexes as Molecular Probes: Intra-and Intermolecular Excited-State Interactions, J. Am. Chem. Soc., 1993, 8230-8238, 115, American Chemical Society.

* cited by examiner

POLYMERS HAVING ATTACHED LUMINESCENT METAL COMPLEXES AND DEVICES MADE WITH SUCH POLYMERS

This application is a divisional of U.S. application Ser. No. 09/974,113, filed Oct. 9, 2001, now U.S. Pat. No. 6,869,693, which claims the benefit of U.S. Provisional Application No. 60/238,934, filed Oct. 10, 2000.

BACKGROUND OF THE INVENTION

1. Field of the Invention

This invention relates to polymeric materials having luminescent metal complexes attached thereto. The invention also relates to polymeric-metal complex salts comprising at least one polymeric material having a plurality of first-type functional groups having a charge, and at least one metal complex having an opposite charge. The invention further relates to electronic devices in which the active layer includes such polymeric materials.

2. Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components. Polymeric materials with stilbenyl or oxadiazole side chains have been reported by Holmes et al., U.S. Pat. No. 5,653,914.

Polymeric light-emitting compounds are frequently insoluble in most common solvents and can be difficult to coat. They are also usually susceptible to degradation when exposed to air and/or moisture, which can complicate the coating process. Small molecule light-emitting materials are usually deposited by evaporative techniques. The equipment required for such processes can be quite expensive and may not be adaptable to continuous processing. Small molecule light-emitting materials can be coated from solution. However, they have a tendency to crystallize with evaporation of the coating solvent, which reduces their electroluminescent effectiveness.

There is a continuing need for electroluminescent compounds having improved efficiency and processes for preparing them.

SUMMARY OF THE INVENTION

The present invention is directed to a polymeric metal complex comprising a polymeric material having a plurality of first-type functional groups, wherein at least a portion of the first-type functional groups are coordinated to at least one metal containing complex. The invention is also directed to a polymeric-metal complex salt comprising a polymeric material having first-type functional groups having a charge and at least one metal complex counterion having the opposite charge. In one embodiment, the metal in the polymeric-metal complex or polymeric-metal complex salt is a lanthanide metal which is further coordinated to a phosphine oxide, N-oxide, or diimine ligand. N-oxides are nitrogen-containing ligands where the nitrogen atom is oxidized by being bound to a single oxygen atom.

In another embodiment, the first-type functional groups in the polymeric-metal complex are selected from phosphine oxides, N-oxides and diimines and the metal is a lanthanide metal which is further coordinated to one or more enolate ligands.

In another embodiment, the first-type functional groups in the polymeric-metal complex salt are substituted ammonium ions and the metal complex counterion is a lanthanide metal which is further coordinated to four enolate ligands.

In another embodiment, the metal in the polymeric metal complex or polymeric metal complex salt is iridium which is further coordinated to a 2-arylpyridine, 2-arylpyrimidine, or 2-arylquinoline.

In another embodiment the metal in the polymeric metal complex or polymeric metal complex salt is Al or Zn and is further coordinated to a Schiff base ligand.

The invention is further directed to an organic electronic device having at least one emitting layer comprising a polymeric metal complex or a polymeric-metal complex salt.

By "coordinated" it is meant that one atom of the functional group forms a bond with the metal atom, where the functional group atom is a Lewis base donor atom, and the metal atom is a Lewis acid acceptor atom. As used herein, the term "compound" is intended to mean bulk material consisting essentially of molecules of the same type. The term "ligand" is intended to mean a molecule, ion, or atom that is attached to a metal ion or atom. The term "complex", when used as a noun, is intended to mean a compound having at least one metal ion coordinated to at least one ligand. The term "group" is intended to mean a part of a compound, such a substituent in an organic compound or a ligand in a complex. The term "moiety" is intended to mean the functional part of a group. The term "functionalized polymer" is intended to mean a polymer having at least one functional group(s) prior to complexation with a metal. The term "precursor metal compound" is intended to mean a metal compound before it is attached to the functionalized polymer. The term "polymeric metal complex" is intended to mean polymeric material containing first-type functional groups where at least a portion of the first-type functional groups are coordinated to at least one metal containing complex. The term "polymeric-metal complex salt" is intended to mean polymeric material having first-type functional groups having a charge and at least one metal complex counterion.

DETAILED DESCRIPTION OF THE PREFERRED EMBODIMENTS

Figure 1:
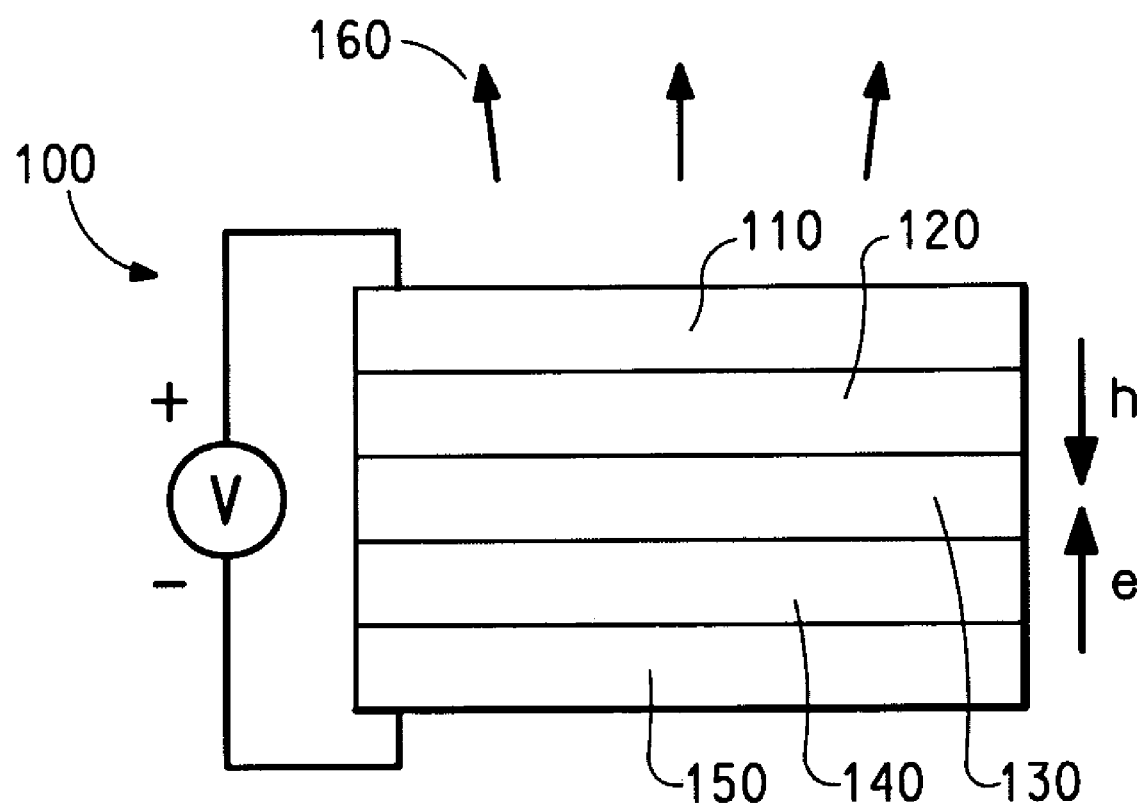
FIG. 1 is a schematic diagram of a light-emitting device (LED).

This invention relates to luminescent polymeric materials comprising a functionalized polymer having a plurality of first-type functional groups, at least a portion of which are associated with metal ions. The metal ions can be associated by coordination. The metal ions are coordinated to the first-type functional groups of the functionalized polymer to form a polymeric-metal complex. The metal ions can also be associated by an ionic bond. Ionic metal complexes of one charge are present as a counterion for functionalized polymers having first-type functional groups of the opposite charge, to form a polymeric-metal complex salt.

In the polymeric-metal complex, the first-type functional group is a group that is capable of coordinating to a metal. Useful first-type functional groups generally contain at least one nitrogen, oxygen, phosphorus or sulfur atom. Examples of suitable first-type functional groups include: carboxylic acid groups, or the acid salt; sulfonic acid groups, or the acid salt; groups having an —OH moiety, such as alkoxyl and phenoxyl; primary, secondary and tertiary amines; imines and diimines, such as pyridine, bipyridine and phenanthroline, and derivatives, including their oxides; phosphines; phosphine oxides; β-dicarbonyl groups, nitriles and isonitriles, cyanates, isocyanates, and any other coordinating groups. Preferred first-type functional groups are carboxylic acid, sulfonic acid, alkoxyl, bipyridine, phenanthroline, and β-dicarbonyl. As used herein, the term "β-dicarbonyl" is intended to mean a neutral compound in which two ketone groups are present, separated by a CHR group. The term "enolate" is intended to mean the anionic form of the β-dicarbonyl in which the H from the CHR group has been abstracted. It should be understood that the composition of a first-type functional group in the functionalized polymer may be identical to or different from the composition of another first-type functional group in the same functionalized polymer.

In the polymeric-metal complex salt, the first-type functional group is a group that has either a negative or positive charge. Examples of negatively charged first-type functional groups include carboxylate ($RCO_2^-$), sulfonate ($RSO_3^-$), enolate$[RC(O)CR'C(O)R'']^{-1}$, alkoxide ($RO^-$), and deprotonated amine ($NRR'^-$), where the various R groups can represent attachment to the polymer, alkyl, aryl, or hydrogen. Examples of positively charged first-type functional groups include ammonium groups having substituents which can be hydrogen, alkyl, aryl, or combinations thereof. Such first-type functional groups can also be selected from any positively charged N-containing heterocyclic group, such as pyridinium.

The metal and coordinated ligands, in the polymeric-metal complex and the polymeric-metal complex salt, are capable of luminescence through metal-to-ligand transitions, metal-metal transitions, or intraligand transitions. Preferred metals are the lanthanide metals, the Group 7, 8, 9, 10 and 11 transition metals, and the Group 12 and 13 metals, using the IUPAC numbering system, numbering the groups from 1–18 (CRC Handbook of Chemistry and Physics, 81$^{st}$ Edition, 2000). Particularly preferred metals are europium, terbium, thulium, rhenium, ruthenium, osmium, rhodium, iridium, platinum, palladium, gold, aluminum and zinc.

In the polymeric-metal complex, the at least one metal ions or atoms are coordinated to a plurality of ligands, at least one of which is the first-type functional group on the functionalized polymer. In the case where luminescence is due to metal-to-ligand transitions, the nature of the other ligands can effect the luminescence strength, wavelength, efficiency and other properties. The other ligands are discussed in more detail below.

In the polymeric-metal complex salt, the metal is coordinated to ligands to form a complex which is ionic, having a charge opposite in sign from the charge on the first-type functional groups. The metal complex is the counterion to the charged functionalized polymer. The metal complex counterion comprises a metal cation and ligands which may or may not be charged. If the charge on the metal exceeds the total negative charge of the ligands, then the complex will be a cation. It can then act as a counterion for a negatively charged polymer. If the total negative charge of the ligands is greater than the positive charge of the metal, then the complex will be an anion. It can then act as a counterion for a positively charged polymer. As with the polymeric-metal complex, when the luminescence is due to metal-to-ligand transitions, the nature of the ligands in the metal complex counterion can affect the luminescent properties. Specific examples of metal complex counterions are discussed below.

Polymeric-metal complexes and polymeric-metal complex salts of the present invention can be obtained from combining at least one functionalized polymer with at least one precursor metal compound.

I. Functionalized Polymer

The functionalized polymeric compounds that are useful in the present invention can be generally described as having: (a) a polymeric backbone; (b) a plurality of a first-type functional group; optionally (c) a spacer group between the polymeric backbone and the first-type functional group; and optionally (d) a plurality of one or more second-type functional group(s). The polymeric backbone can be any polymer or copolymer having the desired properties and processability, and to which the desired first-type functional groups can be attached. Some categories of useful polymeric backbones include polyacrylates and polymethacrylates; polystyrenes; polyesters; polyimides; polyurethanes; polycarbazoles; polyfluorenes; polyvinylenes; polyarylene vinylenes; polyamides, polyvinyl ethers and esters; polycarbonates; polyoxazolines; polyphosphazenes; fluoropolymers; and others, including combinations thereof.

As discussed above, the first-type functional group is either one that is capable of coordinating to a metal (to form a polymeric-metal complex) or a group that is negatively or positively charged (to form a polymeric-metal complex salt).

The number of first-type functional groups in the functionalized polymer, which also can be described as the "density of functional groups", will determine the "maximum loading of the metal complex" (the amount of metal that can be coordinated to the functionalized polymer). For the polymeric materials of the invention, the density of first-type functional groups is determined by the relative proportion of monomers having first-type functional groups ("first-type functional monomers") to monomers not having functional groups ("non-functional monomers") in the polymer. The metal center provides the luminescence in the polymeric materials of the invention, and may also provide charge transport properties. In the absence of any other charge transport materials, it is necessary to have enough of the luminescent metal group to provide a continuous path for charge transport. If other charge transport materials are present, lower loadings of the metal group may be needed. It also should be taken into consideration that not all of the first-type functional groups may be attached to a metal in the final polymeric metal complex. In general, the ratio of first-type functional monomers to non-functional monomers can be in the range of about 100:0 (no non-functional monomers) to 2:98. In the absence of other charge transport materials, it is preferred that the ratio be in the range of 95:5 to 5:95. In the presence of additional charge transport materials, the ratio of first-type functional monomers to non-functional monomers can be in the range of 2:98 to 80:20. The first-type functional group can be attached directly to the polymer backbone, as, for example, the carboxyl group of a polyacrylic acid polymer. However, the metal complexes can be bulky, and it is frequently preferable to have a spacer group between the first-type functional group and the polymeric backbone. Useful spacer groups are those that are chemically stable and do not deleteriously affect luminescence. The spacer group can be a saturated or unsaturated aliphatic group, or an aromatic group. The spacer group can contain heteroatoms, particularly oxygen and nitrogen. In some cases, a spacer group is present because the most readily available monomers for certain first-type functional groups have the spacer group. For example, a convenient monomer for adding sulfonic acid functionality, is 4-styrenesulfonic acid, in which there is a phenyl spacer group. The spacer group generally has 1 to 50 carbon atoms; preferably 5 to 15 carbon atoms. The spacer group can simply provide distance between the polymer backbone and first-type functional group, or it can provide functionality, as discussed below.

The functionalized polymer can also have a second-type functional group. The second-type functional group can be present to modify the physical properties of the final polymeric metal complex or final polymeric metal complex salt. Examples of such types of groups include plasticizing groups, such as alkylene oxide groups, and reactive and/or crosslinkable groups, such as terminal vinyl groups and epoxy groups.

The second-type functional group(s) can also be functional groups that modify or improve the luminescent properties of the final polymeric metal complex or final polymeric metal complex salt. Examples of such second-type functional groups include those which facilitate charge transport and those which alter the color of light emission. Second-type functional groups that facilitate charge transport include hole transport materials, such as those having arylamine moieties or carbazole moieties; and hole and electron transport materials, such as conjugated unsaturated moieties. Second-type functional groups that alter the color of light emission include fluorescent dyes. The second-type functional group can be present in the polymer backbone, in the spacer group attached to the first-type functional group, or in pendant groups separate from the first-type functional group.

The functionalized polymer can be made using monomer(s) having the desired functional group(s), using conventional polymerization techniques. Examples of suitable acrylic monomers include 2-hydroxyethyl methacrylate (hydroxyl functionality); 2-acetoacetoxyethyl methacrylate (β-dicarbonyl functionality); 4-styrenesulfonic acid and salts thereof (sulfonate functionality); acrylic or methacrylic acid (carboxyl functionality); 4-styrenecarboxylic acid and salts thereof (carboxyl functionality); and acrylic monomers having pendant groups with any of the first-type functional groups discussed above. Functional groups can be added to polymeric backbones by reacting a compound having the functional group and a reactive group with a polymer having another reactive group. For example, a compound having the functional group and an acid chloride group can be reacted with a polymer having alkoxyl functional groups, forming an ester linkage. Alternatively, the acid chloride group can be the functional group on a polymer and can be reacted with a compound having an alkoxyl group. A variety of synthetic routes are available in the organic chemistry literature.

II. Precursor Metal Compound

The precursor metal compound is one which will coordinate to, and/or form an ionic bond with, the first-type functional group on the functionalized polymer and provide luminescence in the final polymeric-metal complex, or polymeric-metal complex salt, as the case may be.

In the case of polymeric-metal complex salts, the precursor metal compound is a metal complex ion salt with a simple (non-polymeric) balancing ion. Examples of metal complex cations include $M(diimine)_3^{2+}$, where M is a Group 7–11 transition metal in the +2 oxidation state; and $Ln(\eta^8\text{-}C_8H_8)(HMPA)_3]^+$, where Ln is a lanthanide metal, $C_8H_8$ is 1,3,5,7-cyclooctatetraene and HMPA is hexamethylphosphoramide. The balancing anion in the precursor metal compound can be, for example, halide, acetate, sulfate, or nitrate. Examples of metal complex anions include complexes of lanthanide +3 metals with four negative ligands, such as enolates, carboxylates, sulfonates, alkoxides and amides. The balancing cation can be, for example, Group 1 or 2 cations.

In the case of polymeric-metal complexes, the precursor metal compound can be a simple metal salt, optionally in the presence of additional ligands, or it can be a metal complex. The polymeric-metal complexes of the invention will be described in terms of three representative types of metals: lanthanides, iridium, and aluminum.

1. Lanthanide Metals

It is preferred that, in the polymeric-metal complex, the lanthanide metal is coordinated to at least one ligand selected from a phosphine oxide, a N-oxide, or a diimine. These ligands can be added separately, or they can be present as the first-type functional group on the polymer. The remaining coordination sites are preferably occupied by enolate ligands. As with the other ligands, the enolate ligands can be present separately, or as the first-type functional group on the polymer.

As used herein, the term "phosphine oxide ligand" is intended to mean a ligand having one or more phosphine oxide groups, such as monophosphine oxides, diphosphine dioxides, and the like. The phosphine oxide has a First Formula shown below:

(First Formula)

phosphine oxide has a First Formula shown below:
wherein A is selected from a spacer group attached to a polymeric backbone;

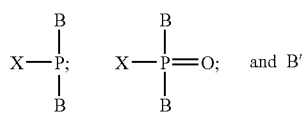
and B' where

B can be different in different parts of the molecule and is $C_6H_nF_{5-n}$ where n is 0 or an integer between 1 and 5

$B'=C_6F_5$ $C=A, B$ $X=(CH_2)_m, (CF_2)_m$, ferrocene m is an integer between 1 and 10.

Examples of suitable monophosphineoxide ligands include:

tris(pentafluorophenyl)phosphine oxide[tpfpO]; (diphenyphosphinomethyl)diphenylphosphine oxide [dppmO]; (diphenyphosphinoethyl)diphenylphosphine oxides [dppeO]; (diphenyphosphinopropyl)diphenylphosphine oxides[dpppO]; (diphenyphosphinobutyl)diphenylphosphine oxides[dppbO]; bis(diphenylphosphinomethyl) phenylphosphineoxide [bisdppmO]; and bis(diphenylphosphinoethyl)phenylphosphine oxide [bisdppeO].

Examples of suitable diphosphine dioxide ligands include:

bis(diphenylphosphino)methane dioxide[dppmO2]; 1,2-bis(diphenylphosphino)ethane dioxide[dppeO2]; 1,3-bis(diphenylphosphino)propane dioxide[dpppO2]; 1,4-bis(diphenylphosphino)butane dioxide[dppbO2]; 1,1'-bis(diphenylphosphino)ferrocene dioxide[dppFeO2]; 1,2-bis(di(pentafluorophenyl)phosphino)ethane dioxide [F5dppeO2]; and bis(diphenylphosphinoethyl)phenyl phosphine dioxides[bisdppeO2].

where the plural term "oxides" is used to indicate that multiple isomers are possible and may be present.

The phosphine oxide ligands are generally prepared by the oxidation of the phosphine analog, as illustrated for a monophosphine oxide in Equation (1) below:

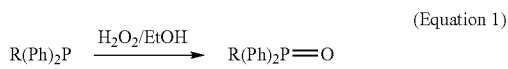

(Equation 1)

If the phosphine analog is not commercially available, it can be made by reacting the lithiated analog with chlorodiphenylphosphine, or by reacting the dihalo analog with lithiated diphenylphosphine. This is illustrated for a diphosphine in Equations (2) and (2a) below:

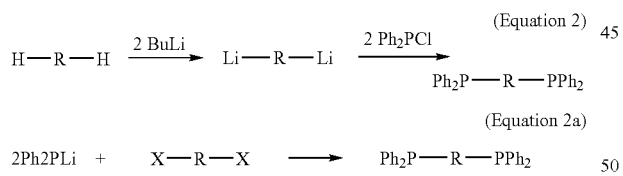

(Equation 2)

(Equation 2a)

The phosphine oxide group can be attached to a polymeric backbone by a variety of synthetic routes available in the organic chemistry literature.

The N-oxide ligand generally has a formula selected from a Second, Third or Fourth Formula below

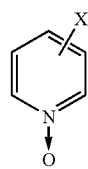

Second Formula

-continued

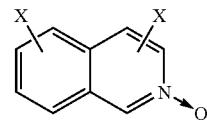

Third Formula

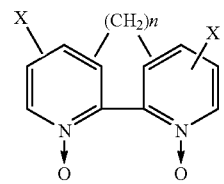

Fourth Formula where

X=attachment to a polymeric backbone, H, R, OR, C(O)OR, CN, OH, halide, where X's can be the same or different from each other $R=C_sH_aF_b$ n is 0 or an integer between 1 and 4;

s is an integer between 1 and 4;

$a+b=2s+1$

Examples of suitable N-oxide ligands include, but are not limited to:

pyridine N-oxide[pyO];

3-cyanopyridine N-oxide[CNpyO]; and bipyridine bis(N-oxide)[bipyO2].

Some N-oxide compounds are commercially available. Others can be made by oxidizing a nitrogen containing ligand with oxidants such as, for example, hydrogen peroxide.

The N-oxides can be attached to a polymeric backbone using known synthetic techniques. In some oases it is possible to attach the nitrogen-containing ligand and then oxidize.

The dilmine ligand preferably has a Fifth Formula, given below:

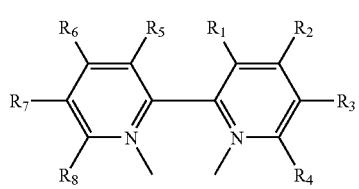

(Fifth Formula)

wherein:

adjacent pairs of $R_1$–$R_8$ can be joined to form a five- or six-membered ring, $R_1$–$R_8$ can be the same or different from each other and are selected from H, alkyl, amy, alkytaryl, $C_nF_{2n+1}$, $OC_nF_{2n+1}$, and $OCF_2X$, where n is an integer between 1 and 6 and X=H, Cl, orbr.

As used herein, the terms "alkyl, aryl and alkylaryl" are Intended to encompass both groups which are unsubstituted and the substituted analogs. Substituent groups can include alkyl, aryl, halogen, $C_nF_{2n+1}$, $OC_nF_{2n+1}$, and $OCF_2X$, where rt is an integer between 1 and 6 and X=H, Cl, or Br.

Examples of suitable diimine ligands are dipyridine ligands having the Fifth Formula and phenanthroline ligands having a Sixth Formula below:

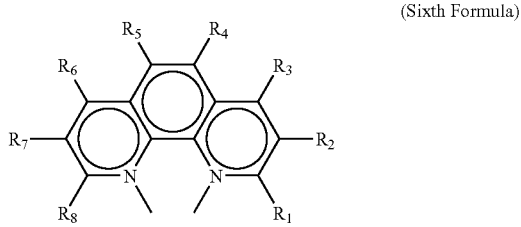

(Sixth Formula)

where $R_1$–$R_8$ are as defined in the Fifth Formula above; and with the substituents given in Table 1.

TABLE 1

| Ligand | Formula | $R_1$ | $R_2$ | $R_3$ | $R_4$ | $R_5$ | $R_6$ | $R_7$ | $R_8$ |
|---|---|---|---|---|---|---|---|---|---|
| 1-a | Fifth | H | H | H | H | H | H | H | H |
| 1-b | Fifth | H | H | $CF_3$ | H | H | $CF_3$ | H | H |
| 1-c | Sixth | H | Ph | H | H | H | H | Ph | H |
| 1-d | Sixth | H | H | Ph | H | H | Ph | H | H |
| 1-e | Sixth | $CH_3$ | H | Ph | H | H | Ph | H | $CH_3$ |

The diimine ligands are frequently commercially available. Derivative compounds can be made by a variety of well-known synthetic routes. The diimine group can be attached to a polymeric backbone by, for example, reacting an acid chloride derivative of the diimine with a polymer having alcohol functional groups. Similarly, a diimine derivative with an alcohol group can be reacted with a polymer having acid chloride groups. A variety of synthetic procedures are available in the organic chemistry literature.

The enolate ligands generally have a Seventh Formula given below:

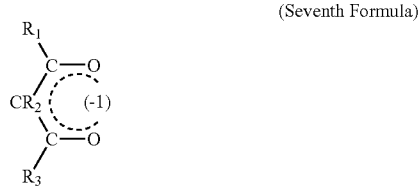

(Seventh Formula)

where $R^1$, $R^2$, $R^3$ are alike or different from each other. The R groups can be hydrogen, halogen, substituted or unsubstituted alkyl, aryl, alkylaryl or heterocyclic groups. Adjacent R groups can be joined to form five- and six-membered rings, which can be substituted, and may be N—, O—, or S—containing heterocyclic rings. Preferred $R^1$ and $R^3$ groups are selected from H, F, $C_nH_aF_b$, $C_6H_5$ which may be substituted with alkyl, aryl, halide, or combinations thereof, $C_4H_3S$, and $C_4H_3O$, where n is an integer between 1 and 6 and a+b=2n+1. Preferred $R^2$ groups are H, $CH_2$-aryl, halide, and $C_nH_aF_b$, where n is an integer between 1 and 6 and a+b=2n+1.

Examples of suitable enolate ligands include the compounds listed below. The abbreviation for the enolate form is given in brackets.

2,4-pentanedionate[acac];

1,3-diphenyl-1,3-propanedionate[DI];

2,2,6,6-tetramethyl-3,5-heptanedionate[TMH];

4,4,4-trifluoro-1-(2-thienyl)-1,3-butanedionate[TTFA];

7,7-dimethyl-1,1,1,2,2,3,3-heptafluoro-4,6-octanedionate [FOD];

heptafluoro-2,4-pentanedionate[F7acac]; and 1-phenyl-3-methyl-4-i-butyryl-pyrazolinonate.

The β-dicarbonyls are generally available commercially.

Heptafluoro-2,4-pentanedione, $CF_3C(O)CFHC(O)CF_3$, can be prepared using a two-step synthesis, based on the reaction of perfluoropentene-2 with ammonia, followed by a hydrolysis step. This compound should be stored and reacted under anyhydrous conditions as it is susceptible to hydrolysis.

2. Iridium

The polymeric-metal complexes with iridium metal are preferably made from precursor iridium compounds which are complexes having at least one ligand, L, which is a 2-arylpyridine, a 2-arylpyrimidine or a 2-arylquinoline. More preferably, the iridium complex has two L ligands. These complexes are frequently referred to as cyclometalated complexes. Ligand L has an Eighth Formula below:

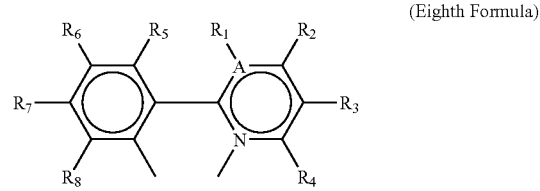

(Eighth Formula)

wherein:

adjacent pairs of $R_1$–$R_4$ and $R_5$–$R_8$ can be joined to form a five- or six-membered ring, and A=C or N, provided that when A=N, there is no $R_1$.

The $R_1$–$R_8$ groups of the Eighth Formula above may be chosen from hydrogen or conventional substitutents for organic compounds, such as alkyl, alkoxy, halogen, nitro, and cyano groups, as well as fluoro, fluorinated alkyl and fluorinated alkoxy groups. The groups can be partially or fully fluorinated (perfluorinated). Preferred ligands L have all $R_1$–$R_8$ substituents selected from hydrogen, fluoro, perfluorinated alkyl ($C_sF_{2s+1}$) and perfluorinated alkoxy groups ($OC_sF_{2s+1}$), where the perfluorinated alkyl and alkoxy groups have 1–6 carbon atoms, or a group of the formula $OCF_2X$, where X=H, Cl, or Br. In a preferred embodiment, at least one of $R_1$–$R_8$ in the eighth formula is selected from F, $C_sH_aF_b$, $OC_sH_aF_b$, and $OCF_2X$, where s is an integer between 1 and 6, a+b=2s+1, and X=H, Cl, or Br.

Examples of suitable ligands L are given in Table 2 below:

TABLE 2

| Ligand | A | $R_1$ | $R_2$ | $R_3$ | $R_4$ | $R_5$ | $R_6$ | $R_7$ | $R_8$ |
|---|---|---|---|---|---|---|---|---|---|
| 2-a | C | H | H | $CF_3$ | H | H | H | H | H |
| 2-b | C | H | H | $CF_3$ | H | H | H | F | H |
| 2-c | C | H | H | $CF_3$ | H | F | H | H | H |
| 2-d | C | H | H | H | H | F | H | H | H |
| 2-e | C | H | H | $CF_3$ | H | H | $CF_3$ | H | H |
| 2-f | C | H | H | H | H | H | $CF_3$ | H | H |
| 2-g | C | H | H | H | H | H | H | F | H |
| 2-h | C | Cl | H | $CF_3$ | H | H | H | H | H |
| 2-i | C | H | H | $CF_3$ | H | H | H | $OCH_3$ | H |
| 2-j | C | H | H | $CF_3$ | H | H | F | H | H |

TABLE 2-continued

| Ligand | A | $R_1$ | $R_2$ | $R_3$ | $R_4$ | $R_5$ | $R_6$ | $R_7$ | $R_8$ |
|---|---|---|---|---|---|---|---|---|---|
| 2-k | C | H | H | $NO_2$ | H | H | $CF_3$ | H | H |
| 2-l | C | H | H | $CF_3$ | H | H | H | $OCF_3$ | H |
| 2-m | N | — | $CF_3$ | H | H | H | H | F | H |

A more preferred precursor iridium complex is an iridium dimer having a Ninth Formula below:

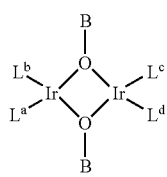

(Ninth Formula)

wherein:

B=H, $CH_3$, or $C_2H_5$, and $L^a$, $L^b$, $L^c$, and $L^d$ can be the same or different from each other and each of $L^a$, $L^b$, $L^c$, and $L^d$ has the Eighth Formula above.

The iridium dimers can generally be prepared by first reacting iridium trichloride hydrate with the 2-phenylpyridine, 2-phenylpyrimidine or 2-phenylquinoline, and adding NaOB.

One particularly useful iridium dimer is the hydroxo iridium dimer, having a Tenth Formula below:

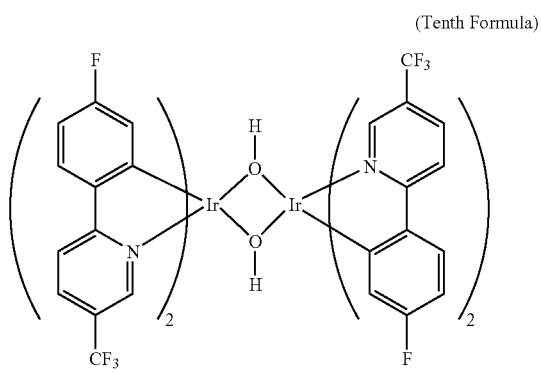

(Tenth Formula)

The substituted 2-phenylpyridines, 2-phenylpyrimidines, and 2-phenylquinolines, are prepared, in good to excellent yield, using the Suzuki coupling of the substituted 2-chloropyridine, 2-chloropyrimidine or 2-chloroquinoline with arylboronic acid as described in O. Lohse, P. Thevenin, E. Waldvogel, Synlett, 1999, 45–48.

3. Aluminum

Preferred precursor aluminum compounds are complexes including a multidentate Schiff base ligand. Schiff bases are compounds that are prepared by a condensation reaction between an aldehyde or ketone derivative and a primary amine. By choosing various different poly-amines and aldehydes or ketones, it is possible to generate a wide array of multidentate anionic ligands. A preferred class of Schiff base ligands has an Eleventh Formula below:

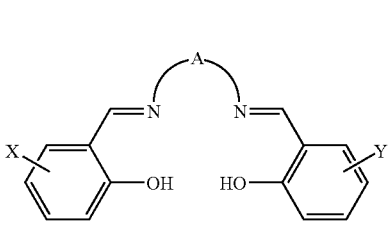

(Eleventh Formula)

where A represents a bridging group derived from the poly-amine reactant, which can be alkyl, cycloalkyl, or aryl; X and Y represent substituents on the phenyl group of the salicylaldehyde reactant, which can be alkyl or aryl groups. Examples of suitable Schiff base ligands are given in Table 3 below.

TABLE 3

| Ligand | A | X | Y |
|---|---|---|---|
| 3-a | 1,2-phenyl | 3,5-di-t-butyl | 3,5-di-t-butyl |
| 3-b | Cis-1,2-cyclohexyl | 3,5-di-t-butyl | 3,5-di-t-butyl |
| 3-c | Trans-1,2-cyclohexyl | 3,5-di-t-butyl | 3,5-di-t-butyl |

One useful precursor aluminum complex can be made by the addition of one molar equivalent of triethylaluminum to the Schiff base compound in hexane or toluene solvent. This forms the ethyl aluminum Schiff base complex.

III. Polymeric-Metal Complexes

The polymeric-metal complexes are generally prepared by adding a precursor metal compound to a functionalized polymer to which it will coordinate. The specific choice of functionalized polymer is dependent on the nature of the precursor metal compound to be added. More than one type of metal can be coordinated to a single functionalized polymer.

A general means of attachment of a metal-ligand precursor complex to a polymeric backbone involves two different approaches. Both require the use of a polymer derivative that contains a Lewis base functionality (X) appended to the primary polymer chain (backbone). This functionality can be (Method A, shown below) the first-type functional group which coordinates directly to the metal, thus making it a ligand in the metal primary coordination sphere (with additional ligands, $L_n$). Alternatively, (Method B, shown below) the polymer functionality can be attached covalently at a proximal site on a ligand (L') that is a component of the primary coordination sphere (with additional ligands, $L_n$).

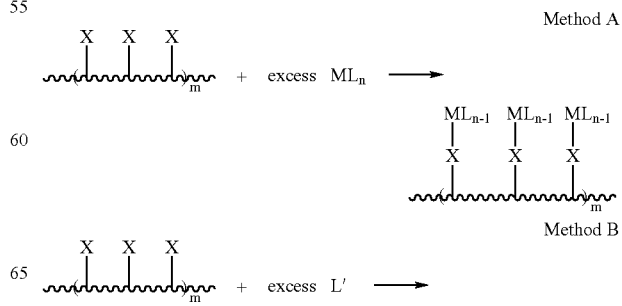

-continued

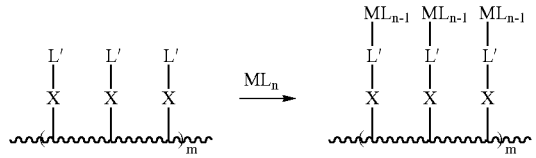

Either method may be used to append any metal-to-ligand charge transfer (MLCT) emitters (including Re-, Ru-, and Os-diimine and Rh-, Ir-, Pd-, and Pt-phenylpyridyl complexes), any intraligand charge transfer emitter complexes (including Al and Zn Schiff base complexes), or any lanthanide (atomic) emitter complexes (including Eu acetylacetonate complexes). For example, the polymer-bound Lewis base could either be directly attached to the metal or be attached via an acceptor functionality appended from a bipyridyl or phenylpyridyl ligand.

This can be illustrated more specifically with the class of [Re(CO)$_3$(2,2'-bipyridyl)L]emitters. A polymer-bound arylsulfonate functionality can be directly coordinated to Re using Method A. Alternatively, Method B can be used to condense a polymer-bound hydroxyethyl functionality with a 2,2'-bipyridyl derivative that has a carboxylic acid functionality appended from a pyridyl carbon atom. The exact reaction conditions vary with the specific materials used. In general, moderate heat is applied, such as refluxing in a solvent with a boiling point of 100° C. or less. The reaction products can then be recovered by standard solvent removal and purification procedures.

The polymeric lanthanide complexes can generally be prepared by the addition of simple metal salts, such as the halide or acetate salts, to polymers having β-dicarbonyl functional groups in the presence of the other phosphine oxide, N-oxide, or diimine ligands. Solvents such as methylene chloride can be used. Alternatively, complexes of the lanthanides with β-dicarbonyls can be added to polymers having diimine functional groups, such as phenanthroline or bipyridine; phosphine oxide functional groups; or N-oxide functional groups.

The polymeric iridium complexes are most conveniently prepared from the precursor iridium dimers, Ninth and Tenth Formulas above, and polymers with β-dicarbonyl functionality. This is illustrated in Equation (3) below:

(Equation 3)

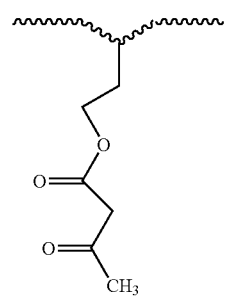

+

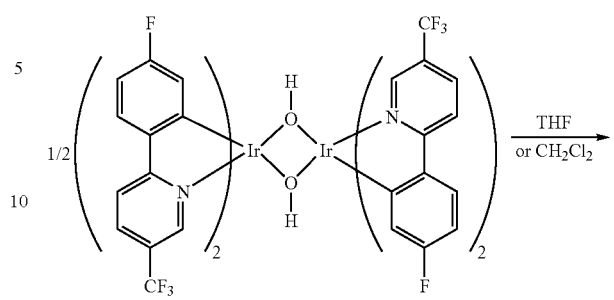

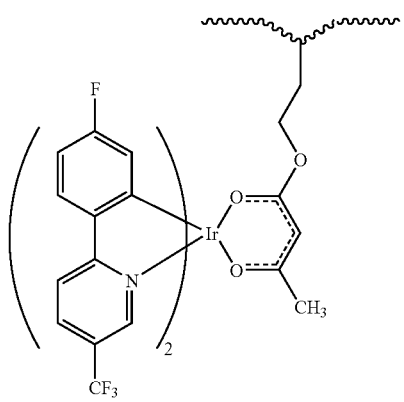

The above reaction rate is very dependent upon the nature of the solvent. In THF it requires several days; in dichloromethane, several hours.

The polymeric aluminum complexes are conveniently prepared from the ethyl aluminum Schiff base precursor complex and an acidic functionalized polymer. This is illustrated in the reaction scheme shown as Equation (4) below:

(Equation 4)

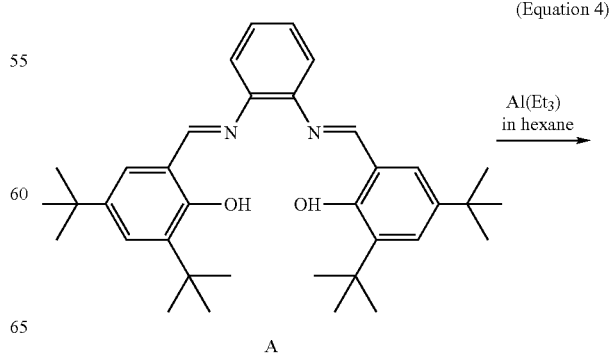

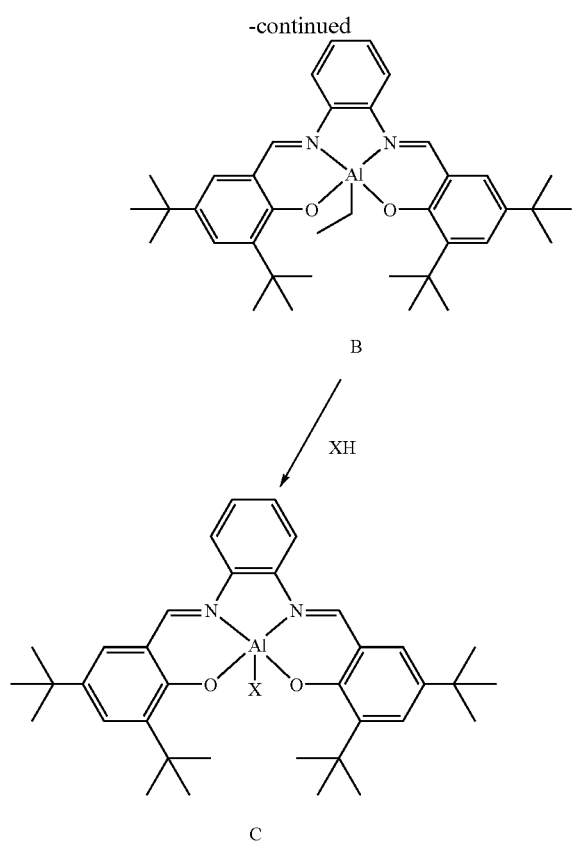

B

↓ XH

C

In this reaction scheme, XH represents the polymer functionalized with a carboxylic or sulfonic acid group. As the ethyl complex reacts with the acid functionality, ethane is evolved and the conjugate base of the polymeric acid (X) becomes bonded to the aluminum.

The polymeric metal complexes of the invention can generally be coated from conventional solvents. The solvent used will depend on the nature of the polymeric backbone. For acrylic polymer backbones, solvents such as tetrahydrofuran, toluene, dimethylformamide, dimethylacetamide, methylene chloride, and ketones, such as acetone, can be used.

IV. Polymeric-Metal Complex Salts

Another route of attaching a precursor metal compound to a functionalized polymer is through the formation of an ionic bond, to form a polymeric-metal complex salt. The polymeric-metal complex salts comprise an ionic form of the functionalized polymer for each corresponding metal complex counterion. The ionic form of the functionalized polymer can have first-type functional groups that are negatively charged or positively charged. Examples of negatively charged first-type functional groups include carboxylate, sulfonate, enolates, alkoxides, and amides. Examples of positively charged first-type functional groups include ammonium groups having substitutents which can be alkyl aryl or both. Such first-type functional groups can also be selected from any positively charge N-containing heterocyclic groups, such as pyridinium. The functionalized polymer can be charged as formed, or can be in a neutral form that can become charged.

The corresponding metal complex counterion comprises at least one metal cation and ligands which may or may not be charged. If the charge on the metal exceeds the total negative charge of the ligands, then the complex will be a cation. It can then act as a counterion for a negatively charged polymer. Examples of metal complex cations include $M(diimine)_3^{2+}$, where M is a Group 7–11 transition metal in the +2 oxidation state; and $Ln(\eta^8-C_8H_8)(HMPA)_3]^+$, where $C_8H_8$ is 1,3,5,7-cyclooctatetraene and HMPA is hexamethylphosphoramide. If the total negative charge of the ligands is greater than the positive charge of the metal, then the complex will be an anion. It can then act as a counterion for a positively charged polymer. Examples of metal complex anions include complexes of lanthanide +3 metals with four negative ligands, such as enolates, carboxylates, sulfonates, alkoxides and amides.

The formation of a polymeric-metal complex salt is illustrated in Equation 5 below for lanthanide dionate compounds:

(Equation 5)

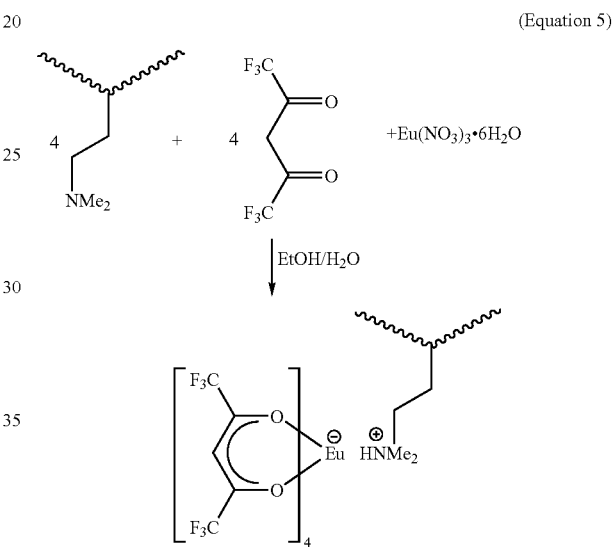

This methodology has previously been reported for monomeric amines in, for example, Melby, L. R.; Rose, N. J.; Abramson, E.; Caris, J. C. *J. Chem. Soc.* 1964, 5117.

Preferred metal complex salts are the salts of tetrakis (enolate) complexes of lanthanide metals; $Ru(bipy)_3^{2+}$, $Os(bipy)_3^{2+}$, $Tb(terpy)_3^{3+}$ $Pt_2(POP)_4^{4-}$, where bipy is bipyridine, and POP is the anhydride of phosphorous acid $((HO)_2P—O—P(OH)_2)$.

V. Devices

Electronic devices of the present invention are useful to exhibit photoluminescent and/or electroluminescent properties. They can be used in light-emitting diodes, which are discussed further below, photodiodes, photodetectors, and as photoconductors, as in xerographic applications.

Light-emitting diodes are referred to as LEDs or, when the active material is organic, as OLEDs. As stated above, OLEDs generally have a structure in which an organic active layer is sandwiched between two electrical contact layers. In a preferred embodiment the organic active layer includes at least an electron transport layer, in addition to the light-emitting layer. OLEDs frequently have additional hole transport and electron transport layers. A typical structure is shown in FIG. 1. The device 100 has an anode layer 110 and a cathode layer 150. Adjacent to the anode is a layer 120 comprising hole transport material. Adjacent to the cathode is an optional layer 140 comprising an electron transport material. Between the hole transport layer and the electron transport layer or cathode is the emitting layer 130. When a voltage is applied as best seen in FIG. 1, the electrons and holes move in the directions indicated by the arrows. The electrons and holes combine in the light-emitting layer to form an excited state, sometimes called an exciton. It is from the excitons that photons 160 are emitted. The exciton can also decay via non-radiative processes. This is known as quenching.

The polymeric-metal complexes of the invention and the polymeric-metal complex salts of the invention are particularly useful as the active material in the emitting layer of an OLED. Additional materials can be present in the emitting layer with the polymeric-metal complex or polymeric-metal complex salt. For example, a fluorescent dye may be present to alter the color of emission. In some cases it is desirable to add materials which facilitate charge transport. The materials can be hole transport materials, electron transport materials or other light-emitting materials which have good transport properties. Here hole transport material is defined as material that can receive a positive charge from the anode and move it through the thickness of the material with relatively high efficiency and small loss. Electron transport material is defined as material that can receive a negative charge from the cathode and move it through the thickness of the material with relatively high efficiency and small loss. Some materials can transport both electrons and holes and are more flexible to use.

To achieve high efficiency in the LED, the HOMO (highest occupied molecular orbital) of the hole transport material should align with the work function of the anode, the LUMO (lowest unoccupied molecular orbital) of the electron transport material should align with the work function of the cathode. Chemical compatibility and processability of the materials are also important considerations in selecting the electron and hole transport materials.

With the polymeric-metal complexes and polymeric-metal complex salts of the invention, it is preferred to use hole transport materials such as N,N'-diphenyl-N,N'-bis(3-methylphenyl)-[1,1'-biphenyl]-4,4'-diamine (TPD) and bis[4-(N,N-diethylamino)-2-methylphenyl](4-methylphenyl)methane (MPMP), and hole transport polymers such as polyvinylcarbazole (PVK), (phenylmethyl)polysilane, poly (3,4-ethylenedioxythiophene) (PEDOT), and polyaniline (PANI); electron and hole transporting materials such as 4,4'-N,N'-dicarbazole biphenyl (BCP); or light-emitting materials with good electron and hole transport properties, such as chelated oxinoid compounds, such as tris(8-hydroxyquinolato)aluminum ($Alq_3$). When a charge transport material is used, the polymeric-metal complex is generally present in about 5–80% by weight, based on the total weight of the layer; preferably 10–50% by weight.

In some cases the precursor metal complexes or metal complex ions may be present in more than one isomeric form, or mixtures of different complexes may be present. It will be understood that in the above discussion of OLEDs, the term "precursor metal compound" or "metal complex ion" is intended to encompass mixtures of compounds and/or isomers.

The other layers in the OLED can be made of any materials which are known to be useful in such layers. The anode 110, is an electrode that is particularly efficient for injecting positive charge carriers. It can be made of, for example materials containing a metal, mixed metal, alloy, metal oxide or mixed-metal oxide, or it can be a conducting polymer. Suitable metals include the Group 11 metals, the metals in Groups 4, 5, and 6, and the Groups 8–10 transition metals, as shown on the periodic table of elements (current IUPAC format). If the anode is to be light-transmitting, mixed-metal oxides of Groups 2, 3, 4, 13 and 14 metals, such as indium-tin-oxide, or a conducting polymer, such as polyaniline, can be used. At least one of the anode and cathode should be at least partially transparent to allow the generated light to be observed.

Examples of hole transport materials for layer 120 have been summarized for example, in Kirk-Othmer Encyclopedia of Chemical Technology, Fourth Edition, Vol. 18, p. 837–860, 1996, by Y. Wang. Both hole transporting molecules and polymers can be used. Commonly used hole transporting molecules are: N,N'-diphenyl-N,N'-bis(3-methylphenyl)-]1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)4,4'-diamine (TTB), and porphyrinic compounds, such as copper phthalocyanine. Commonly used hole transporting polymers are polyvinylcarbazole (PVK), (phenylmethyl) polysilane, poly(3,4-ethylenedioxythiophene) (PEDOT), and polyaniline (PANI). It is also possible to obtain hole transporting polymers by doping hole transporting molecules such as those mentioned above into polymers such as polystyrene and polycarbonate.

Examples of electron transport materials for optional layer 140 include metal chelated oxinoid compounds, such as tris(8-hydroxyquinolato)aluminum ($Alq_3$); phenanthroline-based compounds, such as 2,9-dimethyl-4,7-diphenyl-1,10-phenanthroline (DDPA) or 4,7-diphenyl-1,10-phenanthroline (DPA), and azole compounds such as 2-(4-biphenylyl)-5-(4-t-butylphenyl)-1,3,4-oxadiazole (PBD) and 3-(4-biphenylyl)-4-phenyl-5-(4-t-butylphenyl)-1,2,4-triazole (TAZ). Layer 140 can function both to facilitate electron transport, and also serve as a buffer layer or confinement layer to prevent quenching of the exciton at layer interfaces. Preferably, this layer promotes electron mobility and reduces exciton quenching.

The cathode 150, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, the lanthanides, and the actinides. Materials such as aluminum, indium, calcium, barium, and magnesium, as well as combinations, can be used. Li-containing organometallic compounds can also be deposited between the organic layer and the cathode layer to lower the operating voltage.

It is understood that each functional layer may be made up of more than one layer.

The OLED can be prepared by sequentially depositing the individual layers on a suitable substrate. Substrates such as glass and polymeric films can be used. The organic layers can be coated from solutions or dispersions in suitable solvents, using any conventional coating technique. In general, the different layers will have the following range of thicknesses: anode 110, 500–5000 Å, preferably 1000–2000

Å; hole transport layer 120, 50–1000 Å, preferably 200–800 Å; light-emitting layer 130, 10–1000 Å, preferably 100–800 Å; electron transport layer 140, 50–1000 Å, preferably 200–800 Å; cathode 150, 200–10000 Å, preferably 300–5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

It is understood that the efficiency of devices made with the polymeric-metal complexes and polymeric-metal complex salts of the invention, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The following examples illustrate certain features and advantages of the present invention. They are intended to be illustrative of the invention, but not limiting. All percentages are by weight, unless otherwise indicated. The term "Equiv." in the tables refer to molar equivalents.

Devices

Thin film OLED devices in Examples 31–33 and Comparative Examples A and B were fabricated by spin-coating, and consisted of the following components: an anode, a hole transport layer (HT layer), an electroluminescent layer (EL layer), and a cathode, were fabricated by spin coating. The devices were made and tested in accordance with Procedure 1 or Procedure 2 as described below:

Procedure 1

A substrate of indium tin oxide (ITO) on glass was used, having an ITO thickness of about 1000 to 1500 Å. The HT layer was spin-coated onto the ITO substrate. The HT layer was PEDOT (Baytron® P from Bayer, Germany) at a thickness of 500–1000 Å; polyvinylcarbazole (PVK) at a thickness of about 1000 Å; or a bilayer of PEDOT and PVK at thicknesses of 500–1000 Å and about 1000 Å, respectively. The polymeric metal complex (200 mg) was dissolved in 10 mL toluene (2.0% w/v), filtered through a 0.22 micron filter, and spin-coated at different spin speeds over the HT layer. The thicknesses of resulting films were measured by a TENCOR 500 Surface Profiler.

For the cathode, Ba and Al layers were vapor deposited on top of the EL layers under a vacuum of $1\times10^{-6}$ torr. The final thickness of the Ba layer was 30 Å; the thickness of the Al layer was 3000 Å. Device performance was tested inside a dry box using a calibrated Si photodiode.

Procedure 2

In this procedure, all thicknesses were measured using a Wyco optical intereference profilometer.

A 50 mm×50 mm glass substrate was used having a pattern of indium tin oxide (ITO) pads as an anode. The pads were 3 mm×19 mm in a 2×5 array, 30 ohm ITO. The substrate and anode were cleaned by rinsing with methanol/water, dried and, further cleaned with an oxygen plasma etcher. These were stored under nitrogen atmosphere until used.

The HT layer was PEDOT, purchased as Baytron® P-VP A14083. It was spin coated over the anode/substrate from above as supplied (1.3 wt % solids) at 2000 rpm. The coated HT layer was dried at 110° C. under nitrogen for 15 minutes and cooled under nitrogen. The final thickness was about 80 nm.

The EL layer was spin coated over the dried HT layer, and then dried at about 110° C. The solution concentration and spin speed are given in the examples. In general, a solution at 1 wt % that was spun at 1000–4000 rpm gave a film having a thickness of about 50–100 nm.

A cathode layer of Al was vapor deposited by thermal evaporation over the EL layer to a thickness of 2000 Å, using a 20 mm shadow mask.

To test the devices, contact pads were first formed by cleaning off the organic material in selected areas with solvents. Power was then applied from a DC power supply and the light output was measured with a luminance meter, in $Cd/m^2$. Current/voltage/luminance curves were used to calculate efficiencies in Cd/A.

Control Compounds

In Comparative Examples A and B, the control polymers were polymers having no functional groups. The control complexes were complexes not attached to polymers.

Control Polymer 1 (CP-1)

A copolymer of n-butylmethacrylate (NBMA) and methyl methacrylate (MMA) was prepared by charging the following components listed in Table 4A below to a 1-liter flask equipped with a thermocouple, stirrer, dropping funnels, reflux condenser, and the means for bubbling nitrogen through the reaction.

TABLE 4A

|  | Parts by weight (grams) |
|---|---|
| Portion 1 | |
| n-Butyl methacrylate | 48.0 |
| Methyl methacrylate (MMA) | 2.0 |
| 2,2'-Azobis (2,4-dimethyl valeronitrile): Vazo ®-52 | 1.60 |
| Tetrahydrofuran (THF) | 40.0 |
| Portion 2 | |
| 2,2'-Azobis (2,4-dimethyl valeronitrile): Vazo ®-52 | 5.0 |
| Tetrahydrofuran | 90.0 |
| Portion 3 | |
| n-Butyl methacrylate | 132.0 |
| Methyl methacrylate | 18.0 |
| Tetrahydrofuran | 40.0 |
| Total | 362.82 |

The monomers and the initiator in portion 1 listed in Table 4A above were dissolved in 40 grams of THF in the reaction flask. Nitrogen was sparged through the solution in the reaction flask while heating the solution by a mantle to reach the reflux temperature. Then portion 2 Vazo®-52 initiator dissolved in 90 grams of THF and portion 3 monomers in 40 grams of THF were fed simultaneously into the reaction flask at a uniform rate over 5 hours and 4 hours respectively at reflux temperature. After the initiator, feed (portion 2) was over, the reaction solution was held at reflux temperature for another 60 minutes. Finally the polymer solution was precipitated by adding the polymer solution into excess (2000 grams) of methanol and solvent was decanted. The polymer was rinsed twice with methanol and dried in a vacuum oven for 48 hours at 36° C. The properties are given in Table 4 below.

Control Complex 1 (CC-1)

Eu(TTFA)$_3$ is available commercially. It also can be made according to the procedure in Melby, L. R.; Rose, N. J.; Abramson, E.; Caris, J. C. *J. Am. Chem. Soc.* 1964, 86, 5117.

Control Complex 2 (CC-2)

This control is an iridium complex, not complexed to a polymer, having two ligands derived from the compound in Example 21 below and one acetylacetonate ligand.

A mixture of the iridium hydroxo dimer (100 mg) from Example 22, ethyl acetoacetate (0.075 mL; 4-fold excess), and dichloromethane (4 mL) was stirred at room temperature overnight. The solution was filtered through a short silica plug and evaporated to give an orange-yellow solid which was washed with hexanes and dried. The yield of the complex was 109 mg (94%). $^1$H NMR (CD$_2$Cl$_2$): 1.1 (t, CH$_3$), 3.9 (dm, CH$_2$), 4.8 (s, CH$_3$COCH), 5.9 (m), 6.7 (m), 7.7 (m), 8.0 (m), 8.8 (d). $^{19}$F NMR (CD$_2$Cl$_2$): −63.1 (s, 3F), −63.2 (s, 3F), −109.1 (ddd, 1F), −109.5 (ddd). Analysis: Calcd: C, 44.9; H, 2.6; N, 3.5. Found: C, 44.4; H, 2.6; N, 3.3.

Control Complex 3 (CC-3)

This control is an aluminum complex, not complexed to a polymer, having a ligand derived from the compound in Example 21 below and one sulfonate ligand.

Under a dry nitrogen atmosphere, 0.594 g (1 Mm) ethylaluminum Schiff base from example 22 and 0.186 g (1 Mm) p-ethylbenzenesulfonic acid were mixed in dry tetrahydrofuran. After stirring for 30 mins the solution was evaporated to dryness and the resulting yellow solid was recrystallized from methylene chloride/hexane under dry nitrogen to produce the complex of equation (4) where X=p-ethylbenzenesulfonate.

Examples 1–15

Examples 1–15 illustrate the preparation of the functionalized polymers, and a non-functionalized control polymer. The number average molecular weight (Mn) was determined by gel permeation chromatography (GPC). The polydispersity (PD), by which is meant the ratio of weight average molecular weight (Mw) to Mn, was determined by GPC. A summary of the polymer compositions and properties is given in Table 4 below.

Examples 1–4

These examples illustrate the preparation of a polymer having carboxylic acid functional groups.

Example 1

A copolymer of n-butylmethacrylate (NBMA) and methacrylic acid (MM) was prepared by charging the components listed in Table 5A below to a 1-liter flask equipped with a thermocouple, stirrer, dropping funnels, reflux condenser, and the means for bubbling nitrogen through the reaction.

TABLE 5A

| | Parts by weight (grams) |
|---|---|
| Portion 1 | |
| n-Butyl methacrylate | 48.0 |
| Methacrylic acid | 2.0 |
| 2,2'-Azobis (2,4-dimethyl valeronitrile): Vazo ®-52 | 0.02 |
| Tetrahydrofuran (THF) | 20.0 |
| Portion 2 | |
| 2,2'-Azobis (2,4-dimethyl valeronitrile): Vazo ®-52 | 2.8 |
| Tetrahydrofuran | 100.0 |
| Portion 3 | |
| n-Butyl methacrylate | 132.0 |
| Methacrylic acid | 18.0 |
| Tetrahydrofuran | 40.0 |
| Total | 362.82 |

The monomers and the initiator in portion 1 of Table 5A above were dissolved in 20 grams of THF in the reaction flask. Nitrogen was sparged through the solution in the reaction flask while heating the solution by a mantle to reach the reflux temperature. Then the portion 2 Vazo®-52 initiator dissolved in 100 grams of THF and the portion 3 monomers in 40 grams of THF were fed simultaneously into the reaction flask at a uniform rate over 5 hours and 4 hours respectively at reflux temperature. After the initiator, feed (portion 2) was over, the reaction solution was held at reflux temperature for another 60 minutes. Finally after cooling to room temperature, a portion of the polymer solution (100 grams) was precipitated by adding the polymer solution into excess (300 grams) of petroleum ether and solvent was decanted. The polymer was rinsed twice with petroleum ether and dried in a vacuum oven for 48 hours at 36° C. The polymer yield was 91%.

Examples 2–4

The procedure of Example 1 was repeated using different amounts of monomers.

Examples 5–8

These examples illustrate the preparation of a polymer having β-dicarbonyl functional groups.

Example 5

A copolymer of isobutyl methacrylate (IBMA) and acetoacetoxyethyl methacrylate (AAEM) was prepared by charging the components listed in Table 6A below to a 1-liter flask equipped with a thermocouple, stirrer, dropping funnels, reflux condenser, and the means for bubbling nitrogen through the reaction.

TABLE 6A

| | Parts by weight (grams) |
|---|---|
| Portion 1 | |
| Isobutyl methacrylate (IBMA) | 48.0 |
| 2-(Methacryloyloxy)ethyl acetoacetate (AAEM) | 2.0 |

TABLE 6A-continued

| | Parts by weight (grams) |
|---|---|
| 2,2'-Azobis (2,4-dimethyl valeronitrile): Vazo ®-52 | 1.6 |
| Tetrahydrofuran (THF) | 40.0 |
| Portion 2 | |
| 2,2'-Azobis (2,4-dimethyl valeronitrile): Vazo ®-52 | 5.0 |
| Tetrahydrofuran | 90.0 |
| Portion 3 | |
| Isobutyl methacrylate (IBMA) | 132.0 |
| 2-(Methacryloyloxy)ethyl acetoacetate (AAEM) | 18.0 |
| Tetrahydrofuran (THF) | 40.0 |
| Total | 376.6 |

The monomers and the initiator in portion 1 of Table 6A above were dissolved in 40 grams of THF in the reaction flask. Nitrogen was sparged through the solution in the reaction flask while heating the solution by a mantle to reach the reflux temperature. Then the portion 2 Vazo®-52 initiator dissolved in 90 grams of THF and the portion 3 monomers in 40 grams of THF were fed simultaneously into the reaction flask at a uniform rate over 5 hours and 4 hours respectively at reflux temperature. After the initiator feed (portion 2) was over, the reaction solution was held at reflux temperature for another 60 minutes. Finally after cooling to room temperature, a portion of the polymer solution (100 grams) was precipitated by adding the polymer solution into excess (300 grams) of petroleum ether and solvent was decanted. The polymer was rinsed twice with petroleum ether and dried in a vacuum oven for 48 hours at 36° C. The polymer yield was 46.94%.

Examples 6–8

The procedure of Example 5 was repeated using different amounts of monomers.

Examples 9–11

These examples illustrate the preparation of a polymer having alkoxy functional groups.

Example 9

A copolymer of methyl methacrylate (MMA) and 2-hydroxyethyl methacrylate (HEMA) was prepared by charging the components listed in Table 7A below to a 2-liter flask equipped with a thermocouple, stirrer, dropping funnels, reflux condenser, and the means for bubbling nitrogen through the reaction.

TABLE 7A

| | Parts by weight (grams) |
|---|---|
| Portion 1 | |
| Acetone | 110.0 |
| Portion 2 | |
| Methyl methacrylate | 360.0 |
| 2-Hydroxyethyl methacrylate | 360.0 |

TABLE 7A-continued

| | Parts by weight (grams) |
|---|---|
| Portion 3 | |
| 2,2'-Azobis (2,4-dimethyl valeronitrile): Vazo ®-52 | 6.0 |
| Acetone | 125.0 |
| Total | 961 |

The solvent (acetone) in portion 1 of Table 7A above was added to the reaction flask. Nitrogen was sparged through methanol in the reaction flask while heating the solution by a mantle to reach the reflux temperature. Then portion 3 Vazo®-52 initiator dissolved in 125 grams of acetone and portion 2 monomers were fed simultaneously into the reaction flask at a uniform rate over 5 hours and 4 hours respectively at reflux temperature. To reduce the viscosity of the solution during polymerization, 100 mL of acetone was added each time after feeding (portions 2 and 3): at 98 minutes, 150 minutes, 170 minutes, 217 minutes, 253 minutes and 300 minutes. After the initiator feed (portion 3) was over, the reaction solution was held at reflux temperature for another 60 minutes and then cooled to room temperature to stop the polymerization.

Examples 10–11

The procedure of Example 9 was repeated using different amounts of monomers.

Example 12

This example illustrates the preparation of a different polymer having alkoxy functional groups.

A copolymer of isobutyl methacrylate (IBMA) and 2-hydroxyethyl methacrylate (HEMA) was prepared by charging the components listed in Table 8A below to a 1-liter flask equipped with a thermocouple, stirrer, dropping funnels, reflux condenser, and the means for bubbling nitrogen through the reaction.

TABLE 8A

| | Parts by weight (grams) |
|---|---|
| Portion 1 | |
| Isobutyl methacrylate | 18.0 |
| 2-Hydroxyethyl methacrylate | 2.0 |
| 2,2'-Azobis (2,4-dimethyl valeronitrile): Vazo ®-52 | 1.60 |
| Tetrahydrofuran (THF) | 30.0 |
| Portion 2 | |
| 2,2'-Azobis (2,4-dimethyl valeronitrile): Vazo ®-52 | 5.0 |
| Tetrahydrofuran | 77.0 |
| Portion 3 | |
| Isobutyl methacrylate | 162.0 |
| 2-Hydroxyethyl methacrylate | 18.0 |
| Tetrahydrofuran | 10.0 |
| Total | 323.6 |

The monomers and the initiator in portion 1 of Table 8A above were dissolved in 26 grams of THF in the reaction flask. Nitrogen was sparged through the solution in the reaction flask while heating the solution by a mantle to reach the reflux temperature. Then the portion 2 Vazo®-52 initiator dissolved in 77 grams of THF and the portion 3 monomers in 10 grams of THF were fed simultaneously into the reaction flask at a uniform rate over 5 hours and 4 hours respectively at reflux temperature. After the initiator, feed (portion 2) was over, the reaction solution was held at reflux temperature for another 60 minutes. Finally after cooling to room temperature, a portion of the polymer solution (150 grams) was precipitated by adding the polymer solution into excess of petroleum ether and solvent was decanted. The polymer was rinsed twice with petroleum ether and dried in a vacuum oven for 24 hours at 25° C. The polymer yield was 78.3%.

Examples 13–14

These examples illustrate the preparation of a polymer having sulfonate functional groups.

Synthesis of tetrabutylammonium styrenesulfonate Monomer (SSATBA)

The components listed in Table 9A were combined to make SSATBA.

TABLE 9A

|  | Parts by weight (grams) |
|---|---|
| Portion 1 | |
| Tetrabutylammonium hydrogen sulfate (TBAHS) | 136.09 |
| Deionized water | 120.24 |
| Portion 2 | |
| 4-Styrenesulfonic acid, sodium salt hydrate | 82.64 |
| Deionized water | 330.56 |

The sodium salt of 4-styrenesulfonic acid was dissolved in deionized water (portion 2) in a 2-liter round bottom reaction flask. The TBAHS salt dissolved in deionized water (portion 1) was added over two minutes through a funnel in the reaction flask at 21.8° C. The reaction flask temperature increased to 24.6° C. The clear aqueous solution in the pot became white before the portion 2 addition was completed. The aqueous solution was stirred for 3 hours and in the meantime the solution temperature decreased to 23.2° C. The stirring was stopped and allowed the solution to sit for overnight. During that time, a major portion of the monomer was separated as an oily layer. The oily layer was removed to a separate flask. The remaining aqueous layer was washed twice with about 200 ml of methylene chloride. The methylene chloride washings and the oily layer were combined and rinsed with deionized water. The methylene chloride solution was dried with anhydrous magnesium sulfate. Then the methylene chloride was stripped under vacuum to get the pure tetrabutylammonium styrenesulfonate (SSATBA) monomer as a white solid.

Example 13

A copolymer of isobutylmethacrylate (IBMA) and tetrabutylammonium styrenesulfonate (SSATBA) was prepared by charging the components listed in Table 10A below to a 250 ml flask equipped with a thermocouple, stirrer, dropping funnels, reflux condenser, and the means for bubbling nitrogen through the reaction.

TABLE 10A

|  | Parts by weight (grams) |
|---|---|
| Portion 1 | |
| IBMA | 9.10 |
| SSATBA | 1.70 |
| Methanol | 1.60 |
| 2,2'-Azobis (2,4-dimethyl valeronitrile): Vazo ®-52 | 0.64 |
| Tetrahydrofuran (THF) | 6.30 |
| Portion 2 | |
| 2,2'-Azobis (2,4-dimethyl valeronitrile): Vazo ®-52 | 2.0 |
| Tetrahydrofuran | 19.4 |
| Portion 3 | |
| IBMA | 36.4 |
| SSATBA | 32.3 |
| Methanol | 22.55 |
| Tetrahydrofuran | 7.0 |
| Total | 144.99 |

The monomers and the initiator in portion 1 of Table 10 A above were dissolved in the solvent and added in the reaction flask. Nitrogen was sparged through the solution in the reaction flask while heating the solution by a mantle to reach the reflux temperature. Then the portion 2 Vazo®-52 initiator dissolved in 19.4 grams of THF and the portion 3 monomers dissolved in the solvent were fed simultaneously into the reaction flask at a uniform rate over 5 hours and 4 hours respectively at reflux temperature. During the feeds, whenever the polymer solution became very viscous, a small amount of solvent mixture (methanol and THF) was added. The additional amount of solvent mixture added during the reaction was 67.6 grams. After the initiator feed (portion 2) was over, the reaction solution was held at reflux temperature for another 60 minutes. Finally the polymer solution was precipitated by adding the polymer solution into excess (1000 grams) of petroleum ether and solvent was decanted. The polymer was rinsed twice with petroleum ether and dried under vacuum. The polymer yield was 73.8%.

Example 14

The procedure of Example 13 was repeated using different amounts of monomers.

Example 15

This example illustrates the preparation of a polymer having diimine functional groups.

TABLE 11A

| Component | Amount | MW | Mmol | Equiv. |
|---|---|---|---|---|
| Example 12 polymer | 2.00 g |  | 1.537 | 1.8 |
| 4,4'-COCl-2,2'-bpy | 237.5 mg | 281.10 | 0.845 | 1.0 |
| Et3N | 777 mg | 101.19 | 7.69 | 9 |
| 1,2-dichloroethane | 60 mL |  |  |  |

4,4'-COCl-2,2'-bpy = 4,4'-bis(chlorocarbonyl)-2,2'-bipyridine
Et3N = triethylamine The reaction components listed in Table 11A above were combined in a drybox, then refluxed under nitrogen outside for 2 hours. The acid chloride was taken into solution relatively rapidly upon dissolution. The volatiles were then removed in vacuo. The residue was redissolved in toluene and filtered through celite. The filtrate was evaporated to dryness and dried in vacuo overnight. Yield 1.0 g of a pale yellow solid.

Examples 16–18

These examples illustrate the preparation of a polymer having first-type functional groups which are β-dicarbonyl groups, and second-type functional groups which are charge transport groups.

Example 16

In this example, a vinylcarbazole group was present as a second-type functional group providing hole transport.

A terpolymer of isobutylmethacrylate(IBMA)/9-vinylcarbazole(VC)/acetoacetoxyethyl methacrylate(AAEM) was prepared by charging the components listed in Table 12A below to a 250 mL flask equipped with a thermocouple, stirrer, dropping funnels, reflux condenser, and the means for bubbling nitrogen through the reaction.

TABLE 12A

|  | Parts by weight (grams) |
| --- | --- |
| Portion 1 | |
| Isobutyl methacrylate (IBMA) | 7.21 |
| 9-Vinylcarbazole (VC) | 7.21 |
| 2-(Methacryloyloxy)ethyl acetoacetate (AAEM) | 0.6 |
| 2,2'-Azobis (2,4-dimethyl valeronitrile): Vazo ®-52 | 0.48 |
| Tetrahydrofuran (THF) | 15.0 |
| Portion 2 | |
| 2,2'-Azobis (2,4-dimethyl valeronitrile): Vazo ®-52 | 1.5 |
| Tetrahydrofuran | 32.0 |
| Portion 3 | |
| Isobutyl methacrylate (IBMA) | 19.79 |
| 9-Vinylcarbazole (VC) | 26.9 |
| 2-(Methacryloyloxy)ethyl acetoacetate (AAEM) | 5.4 |
| Tetrahydrofuran (THF) | 18.0 |
| Total | 136.68 |

The monomers and the initiator in portion 1 of Table 12A above were dissolved in 15 grams of THF in the reaction flask. Nitrogen was sparged through the solution in the reaction flask while heating the solution by a mantle to reach the reflux temperature. Then the portion 2 Vazo®-52 initiator dissolved in 32 grams of THF and the portion 3 monomers in 18 grams of THF were fed simultaneously into the reaction flask at a uniform rate over 5 hours and 4 hours respectively at reflux temperature. After the initiator feed (portion 2) was over, the reaction solution was held at reflux temperature for another 60 minutes. Finally after cooling to room temperature, the polymer was precipitated by adding the polymer solution into excess (800 grams) of petroleum ether and solvent was decanted. The polymer was rinsed twice with petroleum ether and dried in a vacuum oven for 48 hours at 50° C. The polymer yield was 95.4%.

Example 17

In this example, a phenanthroline group was present as a second-type functional group providing electron transport.

A terpolymer of isobutylmethacrylate(IBMA)/2-hydroxyethyl methacrylate (HEMA)/acetoacetoxyethyl methacrylate(AAEM) was used as a precursor polymer to attach the electron transport functionality. The IBMA/HEMA/AAEM terpolymer (46.56/46.57/6.87 m/m/m) was prepared by charging the components listed in Table 13A below to a 250 mL flask equipped with a thermocouple, stirrer, dropping funnels, reflux condenser, and the means for bubbling nitrogen through the reaction.

TABLE 13A

|  | Parts by weight (grams) |
| --- | --- |
| Portion 1 | |
| Isobutyl methacrylate (IBMA) | 7.21 |
| 2-Hydroxyethyl methacrylate (HEMA) | 6.6 |
| 2-(Methacryloyloxy)ethyl acetoacetate (AAEM) | 0.6 |
| 2,2'-Azobis (2,4-dimethyl valeronitrile): Vazo ®-52 | 0.48 |
| Tetrahydrofuran (THF) | 15.0 |
| Portion 2 | |
| 2,2'-Azobis (2,4-dimethyl valeronitrile): Vazo ®-52 | 1.5 |
| Tetrahydrofuran | 32.0 |
| Portion 3 | |
| Isobutyl methacrylate (IBMA) | 19.79 |
| 2-Hydroxyethyl methacrylate (HEMA) | 18.12 |
| 2-(Methacryloyloxy)ethyl acetoacetate (AAEM) | 5.4 |
| Tetrahydrofuran (THF) | 18.0 |
| Total | 136.68 |

The monomers and the initiator in portion 1 of Table 13A above were dissolved in 15 grams of THF in the reaction flask. Nitrogen was sparged through the solution in the reaction flask while heating the solution by a mantle to reach the reflux temperature. Then the portion 2 Vazo®-52 initiator dissolved in 32 grams of THF and the portion 3 monomers in 18 grams of THF were fed simultaneously into the reaction flask at a uniform rate over 5 hours and 4 hours respectively at reflux temperature. After the initiator feed (portion 2) was over, the reaction solution was held at reflux temperature for another 60 minutes. Finally after cooling to room temperature, the polymer was precipitated by adding the polymer solution into excess (800 grams) of petroleum ether and solvent was decanted. The polymer was rinsed twice with petroleum ether and dried in a vacuum oven for 48 hours at 50° C. The polymer yield was 99.0%. The molecular weight (Mn) and the polydispersity (Pd) of the terpolymer were 10,284 and 2.15 respectively.

The electron transport group will be attached to the above precursor polymer using the procedure of Example 15. The precursor polymer will be reacted with 5,6-bis(chlorocarbonyl)-4,7-diphenyl-1,10-phenanthroline in the presence of triethylamine. The polymer will be obtained by removing the solvent.

Example 18

In this example, a carbazole group was present as a second-type functional group providing hole transport, and a phenanthroline group was present as a second-type functional group providing electron transport.

A tetrapolymer of isobutylmethacrylate(IBMA)/9-vinylcarbazole/2-hydroxyethyl methacrylate (HEMA)/acetoacetoxyethyl methacrylate(AAEM) was used as a precursor polymer to attach the electron transport functionality.

The IBMA/VC/HEMA/AAEM terpolymer (33.14/30.0/30.0/6.87 m/m/m) was prepared by charging the components listed in Table 14A below to a 250 mL flask equipped with a thermocouple, stirrer, dropping funnels, reflux condenser, and the means for bubbling nitrogen through the reaction.

TABLE 14A

| | Parts by weight (grams) |
|---|---|
| Portion 1 | |
| Isobutyl methacrylate (IBMA) | 4.91 |
| 9-Vinylcarbazole (VC) | 6.04 |
| 2-Hydroxyethyl methacrylate (HEMA) | 4.07 |
| 2-(Methacryloyloxy)ethyl acetoacetate (AAEM) | 1.53 |
| 2,2'-Azobis (2,4-dimethyl valeronitrile): Vazo ®-52 | 0.48 |
| Tetrahydrofuran (THF) | 15.0 |
| Portion 2 | |
| 2,2'-Azobis (2,4-dimethyl valeronitrile): Vazo ®-52 | 1.5 |
| Tetrahydrofuran | 32.0 |
| Portion 3 | |
| Isobutyl methacrylate (IBMA) | 14.31 |
| 9-Vinylcarbazole (VC) | 17.6 |
| 2-Hydroxyethyl methacrylate (HEMA) | 11.85 |
| 2-(Methacryloyloxy)ethyl acetoacetate (AAEM) | 4.46 |
| Tetrahydrofuran (THF) | 18.0 |
| Total | 136.68 |

The monomers and the initiator in portion 1 were dissolved in 15 grams of THF in the reaction flask. Nitrogen was sparged through the solution in the reaction flask while heating the solution by a mantle to reach the reflux temperature. Then the portion 2 Vazo®-52 initiator dissolved in 32 grams of THF and the portion 3 monomers in 18 grams of THF were fed simultaneously into the reaction flask at a uniform rate over 5 hours and 4 hours respectively at reflux temperature. After the initiator feed (portion 2) was over, the reaction solution was held at reflux temperature for another 60 minutes. Finally after cooling to room temperature, the polymer was precipitated by adding the polymer solution into excess (800 grams) of petroleum ether and solvent was decanted. The polymer was rinsed twice with petroleum ether and dried in a vacuum oven for 48 hours at 50° C. The polymer yield was 95%. The molecular weight (Mn) and the polydispersity (Pd) of the terpolymer were 13,123 and 2.47 respectively.

The electron transport group will be attached to the above precursor polymer using the procedure of Example 15. The precursor polymer will be reacted with 5,6-bis(chlorocarbonyl)-4,7-diphenyl-1,10-phenanthroline in the presence of triethylamine. The polymer will be obtained by removing the solvent.

TABLE 4

| Example | Composition molar % | Molecular Weight (Mn) | PD |
|---|---|---|---|
| 1 | nBMA/MAA 85.5/15.5 | 18,347 | 2.69 |
| 2 | nBMA/MAA 47.6/52.4 | 7,691 | 1.87 |
| 3 | nBMA/MAA 85.5/15.5 | 10,302 | 1.92 |
| 4 | nBMA/MAA 47.6/52.4 | | |

TABLE 4-continued

| Example | Composition molar % | Molecular Weight (Mn) | PD |
|---|---|---|---|
| 5 | IBMA/AAEM 93.13/6.87 | 8,712 | 1.9 |
| 6 | IBMA/AAEM 93.13/6.87 | 18,390 | 2.8 |
| 7 | IBMA/AAEM 69.32/30.68 | 17,331 | 2.08 |
| 8 | IBMA/AAEM 69.32/30.68 | 7,749 | 1.82 |
| 9 | MMA/HEMA 56.52/43.48 | 38,361 | 3.11 |
| 10 | MMA/HEMA 30.23/69.77 | 41,258 | 3.18 |
| 11 | MMA/HEMA 79.59/20.41 | 30,308 | 3.07 |
| 12 | IBMA/HEMA 89.17/10.83 | 113,185 | 2.39 |
| 13 | IBMA/SSATBA 80/20 | | |
| 14 | IBMA/SSATBA 90/10 | 116,249 | 2.43 |
| 15 | IBMA/HEMA-bipy 89.17/10.83 | | |
| 16 | IBMA/VC/AAEM 46.56/46.47/6.87 | 11,360 | 2.81 |
| 17 | IBMA/HEMA-phen/AAEM | | |
| 18 | IBMA/VA/HEMA-phen/AAEM | | |
| CP-1 | NBMA/MMA 86.3/13.7 | 9,579 | 1.53 |

Examples 19–20

These examples illustrate the preparation of polymeric-metal complexes of a lanthanide metal.

Example 19

This example illustrates the preparation of a polymeric europium complex in which the first-type functional group is a diimine.

A $CH_2Cl_2$ (10 mL) solution of $Eu(TTFA)_3$ (0.150 g) was added to a $CH_2Cl_2$ (10 mL) solution of Polymer 15 (0.500 g). TTFA is 4,4,4-trifluoro-1-(2-thienyl)-1,3-butanedionate and Polymer 15 is a copolymer of IBMA/HEMA to which a bipyridyl group is attached. The resulting mixture was allowed to stir at room temperature for 48 hours. After the solvent was evaporated, a light-orange sticky solid was obtained (0.440 g). $^{19}F$ NMR ($C_6D_6$): δ−80.62 (major), −78.84 (minor).

Example 20

This example illustrates the preparation of a δpolymeric europium complex in which the first-type functional group is a carboxylic acid.

To a THF (50 mL) solution of Polymer from Example 4 (1.00 g, 28% wt in THF) was added $Eu(NO_3)_3$ (0.72 g, 1.6 mmol) followed by $Et_3N$ (0.22 mL, 1.6 mmol) to give a viscous solution. After stirring the reaction mixture overnight, the solvent was removed by filtration to yield a white solid. This solid was re-dissolved in THF (50 mL) to which was added the β-dicarbonyl form of TTFA (0.72 g, 1.6 mmol) and $Et_3N$ (0.45 mL, 3.2 mmol), and stirred overnight. The resulting polymer was precipitated with hexane, filtered, dissolved in THF (50 mL) and then re-precipitated with hexane. Filtration yielded a fluffy white solid (0.661 g). $^{19}F$ NMR ($CD_2Cl_2$): δ−75.56.

Example 21–23

These examples illustrate the preparation of polymeric-metal complexes of iridium.

Example 21

This example illustrates the preparation of a 2-phenylpyridine compound, 2-(4-fluorophenyl)-5-trifluoromethylpyridine, which is used to form the precursor iridium complex.

The general procedure used was described in O. Lohse, P. Thevenin, E. Waldvogel Synlett, 1999, 45–48. A mixture of 200 ml of degassed water, 20 g of potassium carbonate, 150 ml of 1,2-dimethoxyethane, 0.5 g of Pd(PPh$_3$)$_4$, 0.05 mol of 5-trifluoromethylpyridine, and 0.05 mol of 4-fluorophenyl-boronic acid was refluxed (80–90° C.) for 16–30 h. The resulting reaction mixture was diluted with 300 ml of water and extracted with CH$_2$Cl$_2$ (2×100 ml). The combined organic layers were dried over MgSO$_4$, and the solvent removed by vacuum. The liquid products were purified by fractional vacuum distillation. The solid materials were recrystallized from hexane. The typical purity of isolated materials was >98%. The compound was characterized as follows:

| $^1$H NMR | $^{19}$F NMR | Analysis, % found (calc.) |
|---|---|---|
| 7.08(2H), | −62.75 | C, 60.39(59.75), |
| 7.62(1H), | (3F, s) | H, 3.38(2.90), |
| 7.90(3H), | −111.49 | N, 5.53(5.51) |
| 8.80(1H), | (m) | |

Example 22

This example illustrates the preparation of an hydroxo iridium dimer as a precursor metal complex. The complex was prepared using the 2-(4-fluorophenyl)-5-trifluoromethylpyridine prepared in Example 21, and has the Tenth Formula above.

A mixture of IrCl$_3$·nH$_2$O (54% Ir; 510 mg), 2-(4-fluorophenyl)-5-trifluoromethylpyridine (725 mg), water (5 mL), and 2-ethoxyethanol (20 mL) was vigorously stirred under reflux for 4.5 hours. After a solution of NaOH (2.3 g) in water (5 mL) was added, followed by 20 mL of water, the mixture was stirred under reflux for 2 hours. The mixture was cooled down to room temperature, diluted with 50 mL of water, and filtered. The solid was vigorously stirred under reflux with 30 mL of 1,2-dichloroethane and aqueous NaOH (2.2 g in 8 mL of water) for 6 hours. The organic solvent was evaporated from the mixture to leave a suspension of an orange solid in the aqueous phase. The orange solid was separated by filtration, thoroughly washed with water, and dried under vacuum to produce 0.94 g (95%) of the iridium hydroxo dimer (spectroscopically pure). $^1$H NMR (CD$_2$Cl$_2$): −1.0 (s, 1H, IrOH), 5.5 (dd, 2H), 6.6 (dt, 2H), 7.7 (dd, 2H), 7.9 (dd, 2H), 8.0 (d, 2H), 9.1 (d, 2H). $^{19}$F NMR (CD$_2$Cl$_2$): −62.5 (s, 3F), −109.0 (ddd, 1F).

Example 23

This example illustrates the preparation of a polymeric iridium complex in which the first-type functional group is a β-dicarbonyl.

The hydroxo iridium dimer from Example 22 (167 mg) was added to a THF (5 mL) solution of 90:10 w/w IBMA-AAEM polymer (prepared as described in Example 5; 517 mg). The mixture was stirred for 1 day until all solids dissolved and then kept at room temperature for 6 days. As the reaction occurred, the originally bright orange, poorly photoluminescent solution turned orange-yellow and developed strong photoluminescent (green) properties. Evaporation of the solution and drying the residue under vacuum (2×10$^{-3}$ mm Hg) at 25° C. for 20 hours yielded the product quantitatively, as a homogeneous orange-yellow glassy solid material.

The above procedure resulted in a polymer with 100% attachment of the Ir chromophore to the first-type functional groups (β-dicarbonyls). Similarly, luminescent polymers were prepared with 20%, 25%, and 50% of the acetoacetic ester functionality modified with the Ir complex, by varying the polymer to Ir dimer ratio.

Examples 24–27

These examples illustrate the preparation of polymeric-metal complexes of aluminum.

Example 24

This example illustrates a typical synthesis of a Schiff base ligand. 9.38 g 3,5-di-t-butyl-2-hydroxybenzaldehyde was dissolved into 25 mL methanol and mixed with a solution of 2.3 g 1,2-diaminobenzene also in 25 mL methanol. This mixture was refluxed for 4 hrs during which time a solid yellow precipitate forms. After cooling the solid is collected by filtration and washed with methanol then suction dried to yield 10.6 g (92%). The product structure is illustrated in Equation 4 as material A.

Example 25

A second Schiff base ligand was prepared according to the procedure of Example 24, using 1,2-diaminocyclohexane in place of the diaminobenzene.

Example 26

This example illustrates a typical synthesis of a precursor Al complex, the ethylaluminum Schiff base complex.

2.2 g of the Schiff base ligand from Example 24 was dissolved in dry toluene inside a nitrogen filled glove box. 4 mL of a 1 M solution of triethylaluminum in hexane was then added and the mixture stirred for 1 hr while gently refluxing. The solution was then evaporated to dryness and the orange solid recrystallized from methylene chloride/hexane to give the product in 88% yield and with the structure as illustrated in Equation 4, material B.

Example 27

A second precursor Al complex was prepared according to the procedure of Example 26, using the Schiff base from Example 25.

Example 28

This example illustrates a typical synthesis of polymeric-metal complex in which an Al Schiff base is attached to polymer having sulfonate functional groups.

0.5 g polymer from Example 13 was converted to its acidic form by ion-exchange with a strong acid ion exchange resin in THF/water. 0.395 g of the ethylaluminum Schiff base material from Example 26 was added to a solution of this acidic polymer in 10 mL dry THF under nitrogen and the mixture stirred overnight. The yellow solution became brightly green photoluminescent as the reaction proceeded and ethane gas was slowly evolved. Upon evaporation, a glassy yellow solid was recovered in quantitative yield. The solid was protected from atmospheric moisture until use in spin-coating experiments.

Example 29

A second polymeric-metal complex with an Al Schiff base attached to a polymer having sulfonate functional groups was prepared according to the procedure of Example 27, using the precursor aluminum compound from Example 27.

Example 30

The polymeric-metal complexes from Examples 23, 28 and 29 were used to make devices and tested according to Procedure 1. The results are given in Table 5 below.

TABLE 5

| Polymeric Complex | HT layer | EL layer thickness, Å | Voltage | Peak Radiance, cd/m² |
|---|---|---|---|---|
| Example 23 | PEDOT | 790 | 36 | 0 |
| | PEDOT | 650 | 25 | 0 |
| | PEDOT | 510 | 25 | 157 |
| | PEDOT/PVK | 790 | 60 | 0.4 |
| | PEDOT/PVK | 510 | 25 | 1.0 |
| | PEDOT/PVK | 460 | 20 | 0.3 |
| | PEDOT/PVK | 430 | 20 | 0.3 |
| | PVK | 510 | 45 | 673 |
| | PVK | 510 | 40 | 753 |
| | PVK | 460 | 40 | 925 |
| | PVK | 430 | 40 | 610 |
| Example 28 | PEDOT | 895 | 34 | 11 |
| | PEDOT | 700 | 30 | 122 |
| | PEDOT/PVK | 895 | 55 | 91 |
| | PEDOT/PVK | 700 | 55 | 99 |
| | PEDOT/PVK | 560 | 50 | 17 |
| | PEDOT/PVK | 500 | 50 | 38 |
| | PVK | 560 | 45 | 165 |
| | PVK | 500 | 40 | 75 |
| Example 29 | PEDOT | 820 | 45 | 1.4 |
| | PEDOT | 670 | 46 | 5.4 |
| | PEDOT/PVK | 820 | 67 | 9.7 |
| | PEDOT/PVK | 670 | 60 | 13 |
| | PEDOT/PVK | 670 | 50 | 1.4 |
| | PEDOT/PVK | 560 | 50 | 1.6 |
| | PVK | 670 | 50 | 17 |
| | PVK | 560 | 50 | 21 |

Example 31

The polymeric-metal complex from Example 23 was used as the EL layer in devices made and tested according to Procedure 2. The EL polymeric-metal complex was spun using a 2 wt % solids solution in chlorobenzene. The luminance was about 1 cd/m² at 20 V for EL material spun at 1000 rpm; about 10 cd/m² at 20 V for EL material spun at 4000 rpm.

Comparative Example A

The complex CC-2 (79 mg), control polymer CP-1 (200 mg) and dichloromethane (8 mL) were stirred at room temperature for 2 hours. The solution was evaporated. The concentration of iridium, Ir, constituted 6.8% by weight of the blend, as in Example 23. As the solution was being reduced in volume, solid complex CC-2 precipitated out as a separate crystalline phase. After all volatiles were removed and the solid residue was dried under vacuum, the product was spin-coated from chloroform onto an ITO glass substrate according to Procedure 2. When the coating dried, the iridium complex separated from the polymeric material and formed crystals. This material could not be used to make a device.

Example 32

The polymeric-metal complex from Example 28 was used as the EL layer in devices made and tested according to Procedure 2. The EL polymeric-metal complex was spin-coated using a 2 wt % solids solution in chloroform. The results are given in Table 6 below.

Example 33

Devices were made and tested according to the procedure of Example 32 using the polymeric-metal complex of Example 29. The results are given in Table 6 below.

Comparative Example B

The complex CC-3 was blended with control polymer CP-1 in toluene, so that the aluminum complex constituted 40% by weight of the blend. The total solids content in solution was 1.7 wt %. The blend was used as the EL layer in devices made and tested according to Procedure 2. The results are given in Table 6 below.

TABLE 6

| Example | Spin speed, rpm | Voltage | Peak Radiance cd/m² |
|---|---|---|---|
| 32 | 4000 | 20 | 34 |
| 33 | 4000 | 20 | 0.5 |
| Comparative B | 4000 | 20 | no emission |

Examples 34–35

These examples illustrate the preparation of polymeric-metal complexes of rhenium.

Example 34

In this example the polymeric-metal complex is Re(CO)3(2,2'-bipyridine)(polymer-bound phenylsulfonate).

[Re(CO)$_3$ (2,2'-bipyridine)(THF)](SbF$_6$): This complex will be made according to the procedure for making [Re(CO)$_3$ (2,2'-bipyridine)(MeCN)](PF$_6$) reported in T. J. Meyer & J. Caspar *J. Phys. Chem.* 1983, 87, 952–957, but using AgSbF$_6$ in THF instead of AgPF$_6$ in MeCN.

The polymeric rhenium complex will be made according to the following scheme:

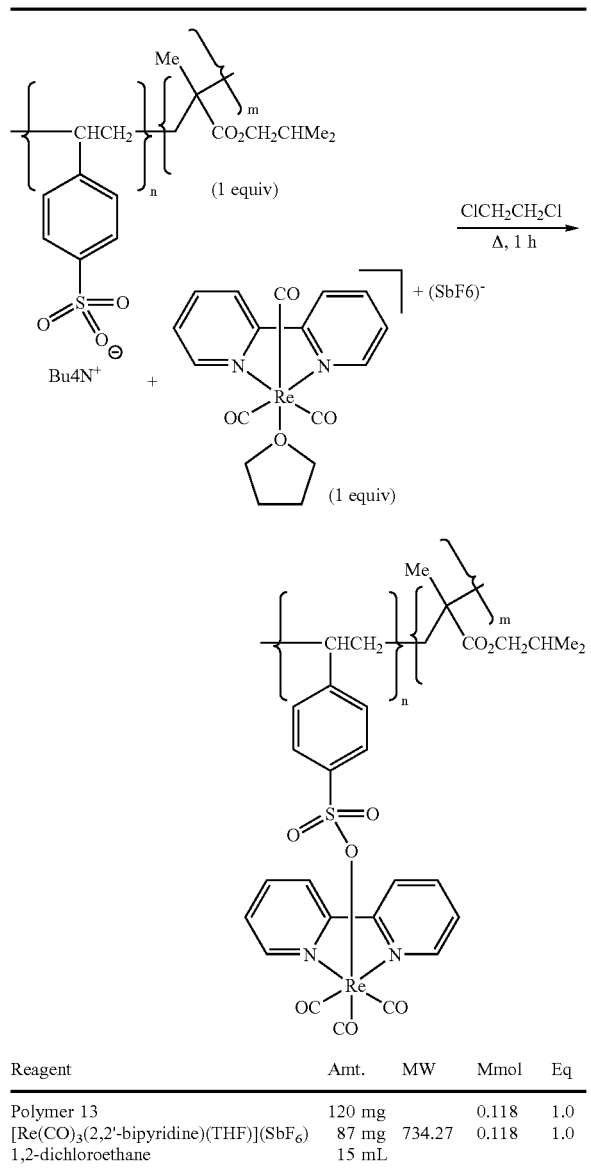

| Reagent | Amt. | MW | Mmol | Eq |
|---|---|---|---|---|
| Polymer 13 | 120 mg | | 0.118 | 1.0 |
| [Re(CO)$_3$(2,2'-bipyridine)(THF)](SbF$_6$) | 87 mg | 734.27 | 0.118 | 1.0 |
| 1,2-dichloroethane | 15 mL | | | |

The reaction components will be combined and allowed to reflux under nitrogen with stirring for 1 hour. Then the volatiles will be removed in vacuo, to afford the desired polymer. The tetrabutylammonium hexafluoroantimonate byproduct will be removed via organic solvent extractions of the crude polymeric rhenium complex.

Example 35

In this examples, the polymeric metal complex is Re(CO)3(polymer-bound-4-carboxy-2,2'-bipyridine)Br.

[Re(CO)$_3$ (2,2'-bipyridine)Br]: This complex will be made according to the procedure for making [Re(CO)$_3$(2,2'-bipyridine)Cl] reported in T. J. Meyer & J. Caspar *J. Phys. Chem.* 1983, 87, 952–957, but using the bromo analog of the starting material.

The polymeric rhenium complex will be made according to the following scheme:

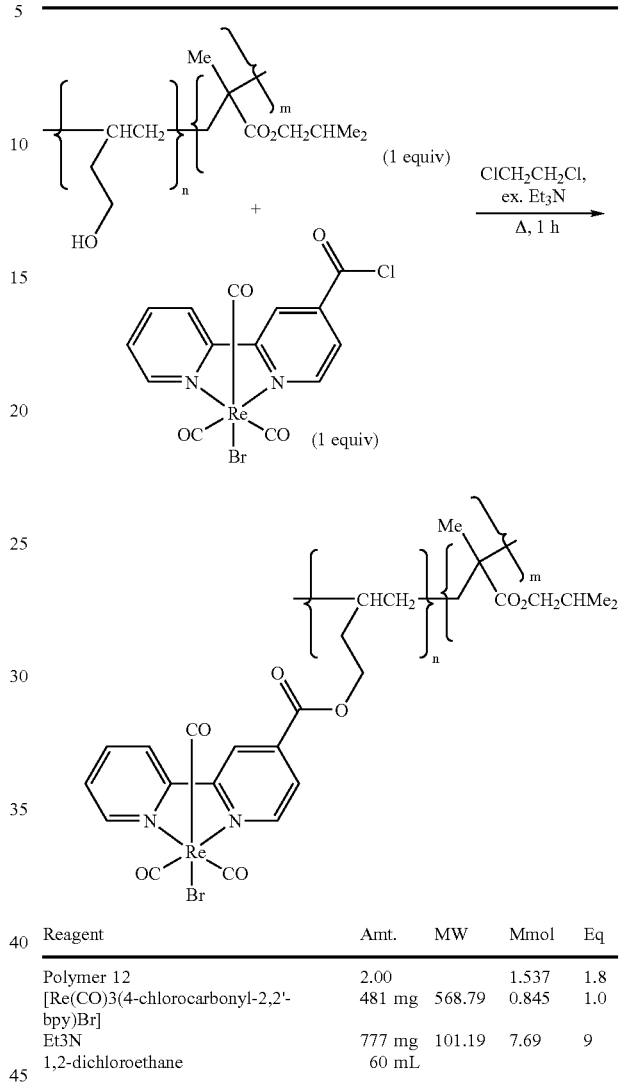

| Reagent | Amt. | MW | Mmol | Eq |
|---|---|---|---|---|
| Polymer 12 | 2.00 | | 1.537 | 1.8 |
| [Re(CO)3(4-chlorocarbonyl-2,2'-bpy)Br] | 481 mg | 568.79 | 0.845 | 1.0 |
| Et3N | 777 mg | 101.19 | 7.69 | 9 |
| 1,2-dichloroethane | 60 mL | | | |

The reaction components will be combined and allowed to reflux under nitrogen with stirring for 1 h. Then the volatiles will be removed in vacuo, to afford the desired polymer. The triethylammonium hydrochloride byproduct will be removed via organic solvent extractions of the crude polymeric rhenium complex.

Example 36

This example illustrates the preparation of a polymeric-metal complex salt, Eu(F6acac)$_4$HNMe$_2$-IBMA/DMAEMA (P12008-108): where F6acac is hexafluoroacetylacetone [CF$_3$C(O)CH$_2$C(O)CF$_3$] Polymer with tertiary amine functionality:IBMA/DMAEMA (60/40 m/m) copolymer The Isobutylmethacrylate(IBMA)/2-(Dimethylamino) ethyl methacrylate (DMAEMA) copolymer was prepared by charging the components listed in Table 15A below to a 2 L flask equipped with a thermocouple, stirrer, dropping funnels, reflux condenser, and the means for bubbling nitrogen through the reaction.

TABLE 15A

| | Parts by weight (grams) |
|---|---|
| Portion 1 | |
| Isobutyl methacrylate (IBMA) | 24.08 |
| 2-(Dimethylamino)ethyl methacrylate (DMAEMA) | 17.76 |
| Acetone | 266.25 |
| Portion 2 | |
| 2,2'-Azobis (2,4-dimethyl valeronitrile): Vazo ®-52 | 14.72 |
| Acetone | 176.63 |
| Portion 3 | |
| Isobutyl methacrylate (IBMA) | 218.18 |
| 2-(Dimethylamino)ethyl methacrylate (DMAEMA) | 159.81 |
| Total | 877.49 |

The monomers in portion 1 of Table 15A above were dissolved in 266.25 grams of acetone in the reaction flask. Nitrogen was sparged through the solution in the reaction flask while heating the solution by a mantle to reach the reflux temperature. Then the portion 2 Vazo®-52 initiator dissolved in 176.63 grams of acetone and the portion 3 monomers were fed simultaneously into the reaction flask. Eighty one point twenty nine percent (81.29%) of initiator solution was fed over two hours and the remaining 18.71% of the initiator solution was fed over 1 hour. The monomer solution was fed uniformly over three hours. After the initiator and the monomer feeds (portions 2 and 3) were over, the reaction solution was held at reflux temperature for another 2 hours. Finally after cooling to room temperature, the polymer was dried by stripping the solvent using a vacuum pump. The polymer yield was 95%.

Polymeric-metal complex salt, Eu(F6acac)$_4$HNMe$_2$-IBMA/DMAEMA

The polymer IBMA/DMAEMA from above (1.00 g) was added to an EtOH (8 mL) solution of F6acac (0.52 g, 2.5 mmol). This mixture was stirred at room temperature for ten minutes to give a clear solution, after which a water (5 mL) solution of EuNO$_3$.6H$_2$O (0.28 g, 0.62 mmol) was added. The resulting mixture was heated to 100° C. until about ~60% of its volume evaporated (via a Dean Stark trap). After removal from heat 50 mL of water was added. This solution showed red photoluminescence.

The polymeric-metal complexes of the invention do not suffer from the above-described processing disadvantages. The polymeric backbone can be chosen to render the complex soluble in a variety of common solvents, as is well known in the art. The backbone polymer is usually soluble in a variety of organic solvents, as is well known in the art. Therefore, the polymeric-metal complexes can also have solubility in the same solvents. The polymeric backbone and the metal complex are generally stable to air and moisture. Crystallization is inhibited when the metal complex is bound to the polymer backbone. In addition, the polymeric backbone can be modified to obtain the desired physical properties of the coating. Since the backbone is not the light-emitting species, changes in its structure have little or no effect on light emission. Furthermore, the bound light-emitting species may be less able to migrate during device operation. This possible decrease in migration can improve device performance and lifetime by maintaining the initial dispersion of the light emitting centers. In the absence of attachment to the polymer backbone, the metal complex emitter species have a tendency to migrate through the emission layer under the influence of the applied electric field. Such migration and aggregation typically has a negative impact on the light emitting properties of the materials. The polymeric-metal complex salts of the invention also are soluble in a variety of common polar solvents, are generally stable to air and moisture, generally do not crystallize because of the bulk of the polymer, and can be modified to obtain the desired physical properties. The metal complex ion is similarly bound and not able to migrate during device operation.

What is claimed is:

1. A polymeric metal complex comprising at least one functionalized polymer having a plurality of a first-type functional group, wherein at least a portion of the first-type functional groups is coordinated to at least one aluminum ion and the at least one aluminum ion is further coordinated to a Schiff base ligand, having the Formula below:

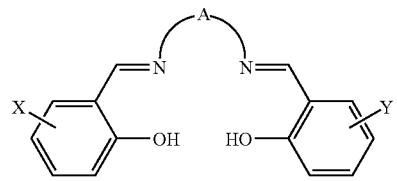

where A is alkylene, cycloalkylene, or arylene, and wherein there may be either one or two of each X and Y and such are the same or different from each other and are selected from alkyl and aryl.

2. A device comprising an emitting layer comprising at least one polymeric metal complex of claim 1.

3. The polymeric metal complex of claim 1 wherein there are two of each X and Y, and each is t-butyl, A is selected from the group consisting of 1,2-phenylene, Cis-1,2-cyclohexylene, and Trans-1,2-cyclohexylene, the two X are at the 3 and 5 positions of the phenyl group to which they are bonded, and the two Y are at the 3 and 5 positions of the phenyl group to which they are bonded.

* * * * *